(12) United States Patent
Stimmeder

(10) Patent No.: US 7,399,483 B2
(45) Date of Patent: *Jul. 15, 2008

(54) CARRIER WITH SOLID FIBRINOGEN AND SOLID THROMBIN

(75) Inventor: Dagmar Stimmeder, Linz (AT)

(73) Assignee: Nycomed Pharma AS, Asker (NO)

( * ) Notice: Subject to any disclaimer, the term of this patent is extended or adjusted under 35 U.S.C. 154(b) by 0 days.

This patent is subject to a terminal disclaimer.

(21) Appl. No.: 11/211,686

(22) Filed: Aug. 26, 2005

(65) Prior Publication Data

US 2006/0193846 A1  Aug. 31, 2006

Related U.S. Application Data

(63) Continuation of application No. 10/702,434, filed on Nov. 7, 2003, now Pat. No. 7,052,713, which is a continuation of application No. 10/054,853, filed on Jan. 25, 2002, now Pat. No. 6,733,774.

(60) Provisional application No. 60/270,914, filed on Feb. 26, 2001.

(30) Foreign Application Priority Data

Feb. 13, 2001 (DK) .............................. 2001 00235

(51) Int. Cl.
A61F 13/00 (2006.01)

(52) U.S. Cl. ..................... 424/443; 424/400; 424/484; 424/486; 424/488

(58) Field of Classification Search .................. 424/400, 424/424, 443, 484
See application file for complete search history.

(56) References Cited

U.S. PATENT DOCUMENTS

| 3,939,831 A | | 2/1976 | Cioca et al. | |
|---|---|---|---|---|
| 4,453,939 A | * | 6/1984 | Zimmerman et al. | 604/368 |
| 4,606,337 A | | 8/1986 | Zimmerman et al. | |
| 4,626,286 A | | 12/1986 | Lubbs | |
| 5,019,087 A | | 5/1991 | Nichols | |
| 5,618,551 A | | 4/1997 | Tardy et al. | |
| 5,660,857 A | | 8/1997 | Haynes et al. | |
| 5,942,278 A | * | 8/1999 | Hagedorn et al. | 427/2.31 |
| 6,177,126 B1 | * | 1/2001 | Hagedorn et al. | 427/2.31 |
| 6,733,774 B2 | | 5/2004 | Stimmeder | |
| 7,052,713 B2 | * | 5/2006 | Stimmeder | 424/443 |

FOREIGN PATENT DOCUMENTS

| EP | 0059265 | | 9/1982 |
|---|---|---|---|
| EP | 0217917 | B1 | 4/1987 |
| EP | 0578823 | A1 | 1/1994 |
| EP | 0664132 | A1 | 7/1995 |
| EP | 0664132 | B1 | 7/1995 |
| EP | 0748633 | A2 | 12/1996 |
| FR | 2668936 | | 5/1992 |
| GB | 1292326 | | 10/1972 |
| JP | 5-213096 | | 8/1993 |
| JP | 7-59812 | | 3/1995 |
| WO | 86/05811 | | 10/1986 |
| WO | 93/19805 | | 10/1993 |
| WO | 94/21739 | | 9/1994 |
| WO | 96/40033 | | 12/1996 |
| WO | 97/28832 | | 8/1997 |
| WO | 97/37694 | | 10/1997 |
| WO | 99/13902 | | 3/1999 |
| WO | 99/56797 | | 11/1999 |
| WO | 99/59647 | | 11/1999 |
| WO | 00/09018 | | 2/2000 |
| WO | 00/15248 | | 3/2000 |
| WO | 00/38752 | | 7/2000 |

OTHER PUBLICATIONS

A. L. Bloom et al., "Physiology of Blood Coagulation" 1990, pp. 14-29.
Torben Halkier, Chapter 5, Activation of prothrombin, pp. 54-70.
Torben Halkier, Chapter 7, Formation and stabilisation of fibrin, pp. 80-103.
Osada et al., "Clinical evaluation of a haemostatic and anti-adhesion preparation used to prevent post-surgical adhesion".
"Mechanisms in blood coagulation, fibrinolysis and the complement system", Cambridge University press 1991; Halkier, Torben, Chapter 24: Haemostasis, pp. 269-282.
Chemical Abstracts of "Microfibrillar and Microcrystalline Collagen I for Medicinal and Pharmaceutical Applications" Columbus, Ohio, U.S., vol. 98, Jun. 13, 1983, No. 24 (English translation).

* cited by examiner

*Primary Examiner*—Michael G. Hartley
*Assistant Examiner*—Rachael Welter
(74) *Attorney, Agent, or Firm*—Wenderoth, Lind & Ponack, L.L.P.

(57) ABSTRACT

The present invention relates to a solid composition useful for tissue gluing, tissue sealing and haemostasis consisting essentially of a) a carrier which has at least one of the following physical properties: elasticity module in the range of 5-100 N/cm, density of 1-10 mg/cm$^3$, chamber diameter of more than 0.75 mm and less than 4 mm and/or having a chamber diameter average below 3 mm and evenly distributed and fixed upon said carrier, b) solid fibrinogen, and c) solid thrombin.

The carrier is a biodegradable polymer such as a polyhyaluronic acid, polyhydroxy acid, e.g. lactic acid, glucolic acid, hydroxybutanoic acid, a cellulose, gelatine or collagen, such as a collagen sponge, e.g. a collagen sponge consisting essentially of collagen type I fibres. The fibrinogen and thrombin are preferably human, purified from a natural source, or transgenic or recombinant human fibrinogen and/or thrombin. In a preferred embodiment the composition does not comprise any antifibronolytic agent such as aprotinin, ε-aminocaproic acid or α2-antiplasmin.

2 Claims, 8 Drawing Sheets

Figure 8. Blood coagulation and degradation of clot and carrier patch. The active components of the coating are shown in grey shaded boxes.

US 7,399,483 B2

CARRIER WITH SOLID FIBRINOGEN AND SOLID THROMBIN

This a Continuation Application of U.S. patent application Ser. No. 10/702,434, filed Nov. 7, 2003 now U.S. Pat. No. 7,052,713, which is a Continuation Application of U.S. patent application Ser. No. 10/054,853, filed Jan. 25, 2002, now U.S. Pat. No. 6,733,774 and claims priority from Provisional Application Ser. No. 60/270,914, filed Feb. 26, 2001.

FIELD OF INVENTION

The present invention relates to a ready-to-use absorbable composition for tissue gluing, tissue sealing and hemostasis consisting essentially of a carrier coated with solidly fixed human components of fibrin glue: human fibrinogen and human thrombin. This fixed combination can be applied directly to e.g. a wound surface. Upon contact with blood, body fluids or physiological saline, the mechanism of this system mimics the final stage of the coagulation cascade, in which thrombin catalyzes the conversion of fibrinogen to fibrin and the activation of factor XIII to give XIIIa. Factor XIIIa, once formed, stabilizes the fibrin clot by covalent cross-linking.

Like a two-component adhesive, wound surface and carrier are glued together by polymerization. During this process, which lasts approximately 3 to 5 minutes, the composition of the invention is preferably pressed onto the wound area. The components of the composition of the invention are degraded enzymatically in about 4-6 months after application.

PRIOR ART

Commercial fibrin glues, that mimic the last step of the coagulation cascade, consist of a highly concentrated fibrinogen solution to be mixed with a thrombin solution before application to the surgical wound exist. These mixtures contain a fibrinolysis inhibitor, e.g. aprotinin or ε-aminocaproicacid, to prevent premature dissolution of the fibrin clot by the fibrinolytic enzyme plasmin. These two-component fibrin glues are valuable in various surgical procedures but may be washed away before hemostasis is achieved if the bleeding is heavy. The two-component fibrin glues furthermore need some preparatory steps including thawing or dissolution. Thus, they are rather impractical and cumbersome to work with and experience is needed for successful use of these fibrin glues.

During the last decade numerous fibrin sealants became the methods of choice in surgery in a number of indications. However, in the majority of trials with fibrin glues a collagen fleece was additionally used to improve hemostatic and adhesive features, indicating their disadvantages and their restrained use by the surgeons.

Collagen has been used as a hemostatic agent since the late sixties. Collagen is the most frequent structural protein in all mammalians. The monomeric protein of approximately 300 kDa (tropocollagen) is covalently crosslinked at specific sites. The mature protein is therefore insoluble and forms characteristic fibrils with high tensile strength. Numerous sub-classes of collagen have been described, the most common of which is collagen type I, the main collagen type in skin, tendons, bones and cornea. Collagen is a fibrous protein consisting of a triple helix with a length of approximately 290 nm. Five of these triple helices (tropocollagen molecules) are staggered to form a microfibril with a diameter of approximately 3.6 nm. These microfibrils have polar and non-polar segments that are readily accessible for specific inter- and intrafibrillar interactions. Microfibrils are packed into a tetragonal lattice to form subfibrils with a diameter of about 30 nm. These subfibrils are then assembled into the collagen fibril, the basic unit of connective tissue, which has a diameter of several hundred nm and is therefore visible in the light microscope as a thin line.

Collagen may be used as a material for sealing wounds, possibly with a coating comprising a fibrin glue. Fibrin glues, i.e. the combination of fibrinogen, thrombin and aprotinin, have successfully been used therapeutically for many years for gluing tissues and nerves and for sealing surfaces when there is minor bleeding. One drawback of the fibrin glues has been that in case of major bleeding the glue is usually washed away before sufficient polymerization of fibrin has occurred. To overcome this problem surgeons have begun applying manually liquid fibrin glues to absorbable carriers such as collagen fleece.

Despite the impressive success of these combined applications this method has not been applied on a broad scale, due to some disadvantages. The preparation is relatively cumbersome, the method requires experience and skilled personnel, and the preparation is not readily available in cases of emergency, the time for preparation being in the range of 10 to 15 min. These factors stimulated the development of an improved product resulting in the development of a fixed combination of a collagen carrier covered with a coating of solid fibrinogen, solid thrombin and solid aprotinin as disclosed in EP 0 059 265.

The function of the collagen carrier disclosed in EP 0 059 265 is mainly that of a carrier which adsorbs and confers mechanical stability to the coagulation preparation with which it is coated.

A product that combines the haemostatic features of fibrin glue with the asset of collagen as a carrier has been developed and manufactured under the trademark TachoComb®. TachoComb® is a ready-to-use and easily applicable fixed combination of a collagen patch coated with the following active components of fibrin glue: human fibrinogen, bovine thrombin and bovine aprotinin.

TachoComb® has been sold since the early 1990s by Nycomed Pharma and has been used in clinical trials in Europe in more than 2500 patients. The product has furthermore been used in more than 700 patients in the Japanese clinical program in a large variety of indications such as liver and lung resections, surgery of the biliary tract, splenic, renal and pancreatic surgery, ENT surgery, gynaecological surgery, and vascular surgery. TachoComb® was found to be effective and safe.

No clinical complications related to the application of TachoComb® have been reported in the course of the clinical trials performed. However, antibodies against aprotinin occurred in three Japanese studies.

A total of only 37 spontaneous adverse drug reactions (ADR) have been reported during years of clinical use of thousands of TachoComb® patches. Sixteen of these ADR's could theoretically be related to reactions against TachoComb® components (fever, pyrexia, eosinophilia, prolonged prothrombin time, hypersensitivity, immunologic or allergic reactions). One ADR (immunologic response) was apparently related to treatment with TachoComb®.

In WO97/37694 (Immuno France S. A.) it is disclosed in reference example 4 that when a collagen product or TachoComb® was used, there was no haemostasis leading to bleeding to death when TachoComb® was used in contrast to haemostasis within 5 minutes when a collagen product without a thrombin content prepared according to WO97/37694 was prepared.

In WO96/40033 the disadvantages of the bovine thrombin used in TachoComb® are emphasized in that the use of bovine or other species of thrombin can introduce harmful viral contamination and possible transmission of bovine diseases, such as bovine spongiform encephalitis.

DETAILED DESCRIPTION

The present invention relates to a solid composition consisting essentially of a carrier which has at least one of the following physical properties
elasticity module in the range of 5-100 N/cm$^2$, such as 10-50 N/cm$^2$;
density of 1-10 mg/cm$^3$, such as 2-7 mg/cm$^3$;
chamber diameter of more than 0.75 mm and less than 4 mm and/or having a chamber diameter average below 3 mm and evenly distributed and fixed upon said carrier
b) solid fibrinogen, and
c) solid thrombin.

The composition may have two, three or all of the above mentioned physical properties. In presently preferred embodiments the carrier material is produced as described in DK PA 2001 00135 and further in the PCT application entitled "A method of preparing a collagen sponge, a device for extracting part of the collagen foam and an elongated collagen sponge" filed by Nycomed Pharma AS on 25 Jan. 2002 claiming priority from said application. In the present context, the term "chamber diameter" should be understood as the largest straight-line wall to wall distance in a chamber, i.e. the largest diagonal straight-line distance of a chamber. The chambers may be of a polygonal shape, such as of an octagonal shape. Thus, when the carrier is cut, the chambers are divided and cut to caverns. The solid fibrinogen and the solid thrombin is fixed to the carrier and most of it is present in the caverns thus providing a substantially even distribution of the solid thrombin and solid fibrinogen. Due to this and the fixation, it is possible to introduce substantial amounts of fibrinogen and thrombin on the carrier in contrast to the situation where liquid compositions of thrombin and fibrinogen are e.g. dropped or sprayed onto the material.

Preparation of Coated Carrier

The preparation of a coated carrier consists essentially of
preparation of a suspension of the active ingredients
even distribution of the suspension to the carrier
drying of the coated carrier to a solid composition/fixation of the active ingredients to the carrier.

Preparation of a suspension with fibrinogen and thrombin comprises:
providing a fibrinogen mixture of fibrinogen and an alcohol, such as ethanol
providing a thrombin mixture of thrombin and an alcohol, such as ethanol
mixing the fibrinogen mixture and the thrombin mixture so as to obtain said suspension.

At the step of providing the mixtures, the mixture may be homogenized or sieved obtaining a suspension containing fibrinogen and thrombin particles with the Folk Ward mean diameter of the particles being 25-100 μm. The temperature is between 0° C. and 12° C.

The carrier may be a collagen carrier, such as a collagen sponge. The collagen sponge may fulfill at least one and preferably a plurality of the following criteria:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most 10$^3$ CFU/g,
collagen content of 75 to 100%,
density of 1 to 10 mg/cm$^3$,
elasticity module in the range of 5-100 N/cm$^2$.

In a presently preferred embodiment, the collagen carrier is produced as described in DK PA 2001 00135. The physical properties of three examples of collagen carriers are provided in the table below:

|  | Example | | |
| --- | --- | --- | --- |
|  | I | II | III |
| pH value | 5.3 | 5.1 | 5.4 |
| Lactic acid content | 2.3% | 2.8% | 2% |
| Ammonium content | 0.1% | 0.2% | 0.1% |
| Soluble protein content | 0.04% | 0.05% | 0.08% |
| Sulphate ashes content | 0.3% | 0.3% | 0.3% |
| Microbiological purity (CFU/g) | <12-345 | <18-124 | <11-33 |
| Collagen content related to dry mass | 95% | 95% | 98% |
| Water content | 14% | 15% | 16% |
| Elasticity modul | 10.4-42.1 N/cm$^2$ | 15-50 N/cm$^2$ | 12.3-41.0 N/cm$^2$ |
| Pore size (diameter; mean value) | 2.9 mm | 2.1 mm | 2.9 mm |
| Density | 2.9-5.3 mg/cm$^3$ | 2.9-5.9 mg/cm$^3$ | 2.4-5.0 mg/cm$^3$ |

Even distribution of the suspensions is carried out either using a drip-on-device as disclosed in U.S. Pat. Nos. 5,942,278 and 6,177,126 or an applicator comprising at least one jet may be used for applying the suspension to the carrier. The jet applicator is forcing the suspension through the jet while the carrier and the jet are moved relatively to each other. The applicator may comprise or be arranged near a conveyor belt, a stirring unit connected to a pump or a system of pumps or another supplying equipment, and a jet or a system of jets which moves transversely, e.g. at right angles to the conveyor belt. Depending on the specific characteristics of the media, the jet or the system of jets may have various shapes and sizes. The jet or the system of jets may be connected to the supplying equipment via tubes. The supplying equipment may promote the coating medium from the stirring unit to the jet systems. During the coating process the jet system may move across the carrier. In its waiting position it may hold on one side of the conveyor belt. The coating process may be initiated by a light barrier sensing the presence of a carrier on the conveyor belt, and may likewise be stopped by a light barrier signal. Such an applicator confers a relatively small dead volume, and it is easy to handle, including easy to clean. Furthermore, it confers the possibility to interrupt the coating process at any time, it is applicable in a relatively broad range of viscosities, and it confers a homogenous coating.

Both systems are applying a volume of 0.08 ml-0.12 ml of suspension pr. $cm^2$ carrier.

An important step is the drying of a suspension of fibrinogen, thrombin and an alcohol applied as a wet coating on a coating surface of a carrier. An example of a method comprises the step of submitting the coated carrier to a pressure below 1000 mbar, so as to obtain a dried coating surface on the carrier and fixate the dried coating to the coating surface. By applying a vacuum and using the vacuum in the drying process, a low temperature (2-10° C.) and a high relative humidity (80-95%) may be kept, whereby the structure and the physical properties of the carrier, in particular a carrier in the form of a collagen, such as a collagen sponge, as well as of the fibrinogen and thrombin may be maintained.

By the term "consisting essentially of" is meant that the three components are all essential and necessary for the invention. However, inessential additives such as calcium ions and a coloring marker such as riboflavin can also be present in the composition. The composition may further comprise other useful ingredients such as one or more pharmaceutical active substances which may e.g. be selected from the group consisting of antibiotic, such as antibacterial or antimycotic, and antineoplastic agents.

Although the carrier material is preferably a collagen sponge which comprises collagen type I material from mammalian, transgenic or recombinant sources, it may be produced by means of other types of collagen i.e. collagen type I, II, III, IV, VII and X. However, it is also envisaged that the carrier may be a biodegradable polymer such as a polyhyaluronic acid, polyhydroxy acid, e.g. lactic acid, glucolic acid, hydroxybutanoic acid, a cellulose, or gelatine.

In a preferred embodiment of the invention, the composition comprises a carrier which has one or more active sides wherein fibrinogen is present in an amount of 2-10 $mg/cm^2$ such as 4.3-6.7 $mg/cm^2$, preferably about 5.5 $mg/cm^2$, and thrombin is present in an amount of 1.0-5.5 $IU/cm^2$, preferably about 2.0 $IU/cm^2$. The fibrinogen and/or thrombin is preferably human, e.g purified from a natural source by methods known to the person skilled in the art, or transgenic or recombinant human fibrinogen and/or thrombin produced by methods known to the person skilled in the art.

The prior art products such as TachoComb®, Beriplast® and TissueSeal® all contain aprotinin or similar anti-fibrinolytic agents. Aprotinin can only be provided from a bovine source. It has been an object of the present inventors to develop a composition with an improved carrier material and only components of human, recombinant or transgene origin. Therefore, developments have been made with respect to the carrier material and it has been investigated whether it was possible to replace the bovine thrombin with human thrombin and to avoid the aprotinin. The present inventors have worked towards this goal through a two-step process.

First of all, TachoComb H has been developed as a follow-up product of TachoComb® with e.g. the bovine thrombin being replaced by human thrombin. Clinical experience with TachoComb H has been performed with regard to a number of therapeutic confirmatory (phase IIIa) clinical trials within the indications hemostasis, tissue gluing and tissue sealing. The yet unpublished results gained in these studies confirmed the efficacy and safety of TachoComb H in the control of blood and air leakage, thus serving as an adjuvant therapy to suturing in hemostasis, tissue gluing and tissue sealing during surgery. In particular, the efficacy of TachoComb H in achieving local hemostasis, expressed as a significant reduction in time-to-hemostasis compared to controls, was convincingly shown in vascular and liver surgery alike.

Also, it has been found that TachoComb H may be able to reduce pulmonary defects in size, resulting in a more rapid resolution of air leakage and may be useful in sealing severe pulmonary leaks and in emphysematous lungs.

However, TachoComb® and TachoComb H both comprise aprotinin as an integral part of the product. Aprotinin has been considered necessary to inhibit possible conversion of small amounts of plasminogen to plasmin in the fibrinogen component and to prevent premature lysis of the fibrin clot especially under hyperfibrinolytic conditions.

The present inventors devised new experiments in order to test this hypothesis that aprotinin was necessary. The in vitro experiments showed the antifibrinolytic protection of aprotinin in the clot and that TachoComb® without aprotinin (TachoComb S) was not dissolved within a very short time. Therefore stressful animal models were designed and TachoComb S was compared to TachoComb H to prove similar efficacy. In all models TachoComb H or S, respectively, was used as only means of hemostasis.

Four extensive experimental series have been performed in order to investigate the efficacy and histopathological pattern of the presently preferred embodiment of the present invention TachoComb S compared to TachoComb H. TachoComb S or TachoComb H were applied on the organs liver, spleen, pancreas or brain/meninges of dogs, pigs or rabbits. The experiments were designed in a way to resemble normal surgical conditions, severely stressful conditions and hyperfibrinolytic conditions.

The results obtained in these four studies did not show any relevant difference between TachoComb S and TachoComb H. Both products behaved similarly with regard to haemostatic and wound sealing efficacy including severely stressful conditions like increased intraorgan pressure or hyperfibrinolysis induced by local r-tPA application.

It can be concluded that the preclinical program designed to evaluate the overall necessity of aprotinin as a component of TachoComb H has proven similar efficacy of TachoComb H and TachoComb S. Both products have been used successfully as only means of hemostasis, tissue gluing and tissue sealing under all experimental conditions. In the course of animal experiments, there were no undesirable tissue reactions. Consequently, aprotinin has been eliminated from the composition of the invention.

The composition of the invention is expected clinically to exert the same hemostatic, tissue gluing and tissue sealing properties as its predecessors and to have the same or an even more satisfactory safety profile. The absence of aprotinin which is presently only available from bovine sources adds safety against hypersensitivity reactions. In this regard it should be noted that antibodies against aprotinin occurred in three Japanese studies. No such immunological response is anticipated with a composition without aprotinin.

In a presently preferred embodiment, the invention relates to a composition for haemostasis, tissue sealing and tissue gluing which comprises a flexible carrier which has at least one of the following physical properties:

elasticity module in the range of 5-100 $N/cm^2$, such as 10-50 $N/cm^2$;

density of 1-10 mg/cm$^3$, such as 2-7 mg/cm$^3$;
chamber diameter of more than 0.75 mm and less than 4 mm and/or having a chamber
diameter average below 3 mm
and which further comprises
solid fibrinogen
and solid thrombin
and does not comprise any antifibronolytic agent such as aprotinin, ε-aminocaproic acid, or α2-antiplasmin,
the solid fibrinogen and solid thrombin being fixed to the carrier in a manner so that the abrasion is less than 1.0 mg/cm$^2$ when a sample of the coated material is shaken on a Vibrofix shaker at a frequency of about 1000 rpm for 2 minutes and
if the coated carrier material is inserted into endoscopic equipment and thereafter removed, the material is substantially unchanged and has cast coating material less than 20% as an indication of the flexibility of the carrier and the solid adhesion of the solid fibrinogen and solid thrombin, and
the material being substantially air tight and liquid tight and having an elasticity factor of at least 1.25 as determined by a test comprising fixation of the coated carrier to a Latex sheet, expansion of the Latex by pressure three times and at the third time measuring the area of the coated carrier at the highest point of Latex sheet expansion and comparing the expanded area of the coated carrier with the starting area of the coated area.

The preferred composition of the invention wherein the fibrinogen and thrombin are human, e.g. purified from a natural source or transgenic or recombinant human fibrinogen and thrombin, is the only non-bovine fibrin sealant available with a fixed combination of active components coated on a flexible carrier and has several advantages:

Ready-to-use, no time consuming thawing or preparation procedure needed
Easily applied directly onto most tissue and organ surfaces
Endoscopic application possible
No problems with the hemostatic running off or being rinsed off the target area
Combination of the gluing effect of fibrin clotting and the mechanical support of the flexible carrier
Highly flexible and withstanding heavy stretching and compression
Effective hemostasis and tissue sealing within 3-5 minutes
Favorable safety profile, i.e. no bovine components
Biodegradable leaving only minor tissue scars
Can be stored at +2° C. to +8° C. and will have an expected shelf life of 36 months,
or at room temperature for a period of up to at least 2 years.

The reason to develop the preferred composition of the invention derives from a wish to get rid of the last bovine component in order to prevent any, even theoretical, risk of transmittance of diseases from cows to humans, including transmissible spongiform encephalopathies (TSEs). The active components fibrinogen and thrombin are thus of human origin, and bovine aprotinin, the inhibitor of the fibrinolytic enzyme plasmin, has been removed. Thus, the advantage of the preferred composition of the invention containing no bovine components is that the risk of transmitting diseases, including bovine spongiform encephalopathy (BSE), via bovine material has been eliminated.

Similarly to other fibrin glues, the composition of the invention works by reproducing the last step of the blood coagulation cascade. A mixture of fibrinogen and thrombin forms a fixed solid layer on the surface of the flexible carrier. Upon contact with fluids, e.g. a bleeding surface, body fluids or physiological saline, the components of the layer dissolve, diffuse into the cavities of the wound and start to react.

The polymerization process produces a strong adhesion between wound surface and carrier patch. During the time required for gluing, i.e. 3 to 5 minutes, the composition of the invention should preferably be pressed gently onto the wound surface. The carrier patch provides mechanical support that allows tamponage of the wound. The patch keeps the coagulation components in place when wounds are bleeding profusely and prevents potential re-bleeding. The mechanism of action involves the conversion by thrombin of fibrinogen into fibrin by splitting off peptides. Fibrin monomers polymerize spontaneously into fibrin strands forming a viscous and elastic clot, which glues the carrier patch to the wound surface. The fibrin matrix subsequently serves as scaffolding for fibrinoblast migration (FIG. 8).

Like a two-component adhesive, wound surface and carrier are glued together by polymerization. The mechanical stability of the carrier patch adds a tamponade effect to the hemostatic effect of fibrin clotting. Further, the active substances are only present on the carrier surface facing the wounded area and by virtue of the tamponade effect and the gentle pressure they do not diffuse through the carrier. Consequently, and in contrast to the situation when using most fibrin glues, there is no adhesion between the wounded area covered with the composition of the invention and other organs or parts thereof when the composition of the invention has been used.

Unlike cyanoacrylate and gelatine-resorcin-formaldehyde (GRF) glues, which are highly histotoxic to parenchymatous tissue, the solid composition of the present invention is physiologically degraded and replaced by tissue within weeks or months after application mainly via two mechanisms:

1. The fibrin clot is degraded partly by fibrinolysis and partly by cellular phagocytosis.
2. The carrier is degraded layer by layer by absorptive granulation tissue and converted into a pseudo-capsule consisting of endogenous connective tissue.

The composition of the invention is useful for hemostasis, tissue gluing and tissue sealing, in particular in surgical intervention in the gastrointestinal system, such as the esophagus, stomach, small intestine, large intestine, rectum, on parenchymal organs, such as liver, spleen, pancreas, kidneys, lungs, adrenal glands, thyroid and lymph nodes, cardiovascular surgery, thoracic surgery including surgery on the trachea, bronchi or lungs, surgical interventions in the ear, nose and throat (ENT) area including dental surgery, gynaecological, urological, bone (e.g. spongiosa resection), and emergency surgery, neurological surgery, lymphatic, biliary, and cerebrospinal (CSF) fistulae, and air leakages during thoracic and pulmonal surgery. The present invention thus also relates to the use of the described compositions for the above purposes.

It should be emphasized that the composition of the invention is substantially air tight and liquid tight which is the reason for the product being particularly useful to treat lymphatic, biliary, and cerebrospinal (CSF) fistulae, and air leakages during pulmonary and thoracic surgery. Further, due to the product being substantially liquid tight, it is highly useful in surgery of highly bleeding organs such as the liver and spleen, and for surgery e.g. in the gastrointestinal channel.

The product of the invention is to be applied when bleeding, or lymphatic, biliary, air or CSF leakage cannot be controlled with conventional methods or when these methods would yield unfavorable results.

The carrier is preferably a collagen sponge, fleece or patch which terms are used synonymously in the present specification and claims. The components collagen, fibrinogen and thrombin are preferably of mammalian origin. Preferably, the solid components are of human origin. The collagen, fibrinogen and thrombin may either be purified from a natural source or recombinant or transgenic human fibrinogen and/or thrombin.

A presently preferred source of collagen is equine. In order to prevent virus transmission due to contamination with equine viruses that are pathogenic to humans by virtue of the collagen patch, appropriate selection of source material and inactivation of potentially pathogenic agents by the manufacturing process is important as precautionary measures.

BRIEF DESCRIPTION OF THE DRAWINGS

FIG. 1.2 illustrates coated Opraskin® and its insertion into endoscopic equipment;

FIG. 1.3 illustrates coated Opraskin® unfolded after insertion into endoscopic equipment;

FIG. 2.2 illustrates coated Willospon® forte and its insertion into endoscopic equipment;

FIG. 2.3 illustrates coated Willospon® forte unfolded after insertion into endoscopic equipment;

FIG. 3.2 illustrates coated Willospon® Spezial inserted into endoscopic equipment;

FIG. 3.3 illustrates coated Willospon® Spezial that is unfolded after insertion into endoscopic equipment;

FIG. 4.2 illustrates the coated Ethisorb® Patch and its insertion into endoscopic equipment;

FIG. 4.3 illustrates coated Ethisorb® Patch that is unfolded after insertion into endoscopic equipment;

FIG. 5.2 illustrates coated Tabotamp® NU Knit and its insertion into endoscopic equipment;

FIG. 5.3 illustrates coated Tabotamp® NU Knit that is unfolded after insertion into endoscopic equipment;

FIG. 6.2 illustrates coated Sponge Nycomed (lab sample) and its insertion into endoscopic equipment;

FIG. 6.3 illustrates coated collagen Sponge Nycomed (lab sample) that is unfolded after insertion into endoscopic equipment;

FIG. 6.3 illustrates coated collagen Sponge Nycomed (production sample-TachoComb®) that is unfolded after insertion into endoscopic equipment;

EXAMPLES

Figure 1:
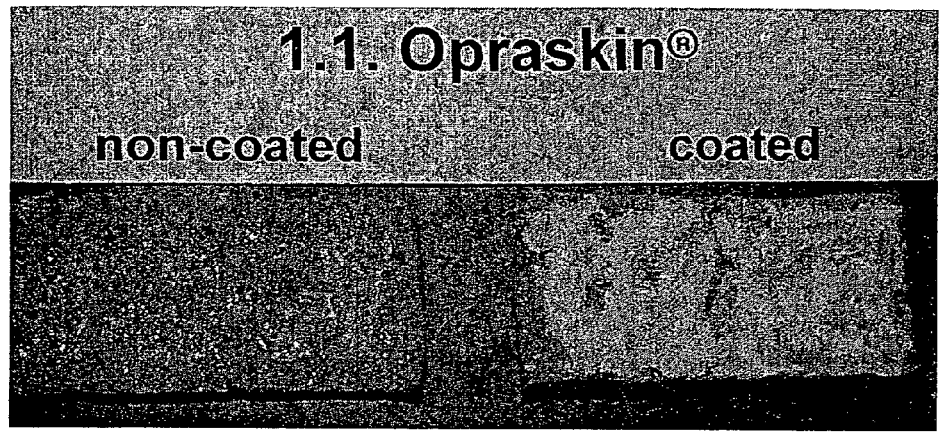
FIG. 1.1 illustrates Opraskin® in both non-coated and coated states.
Figure 1:
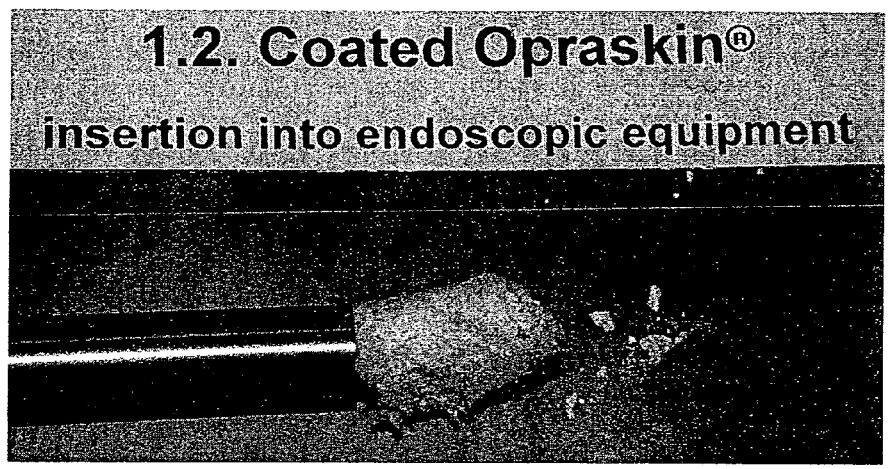
Figure 1:
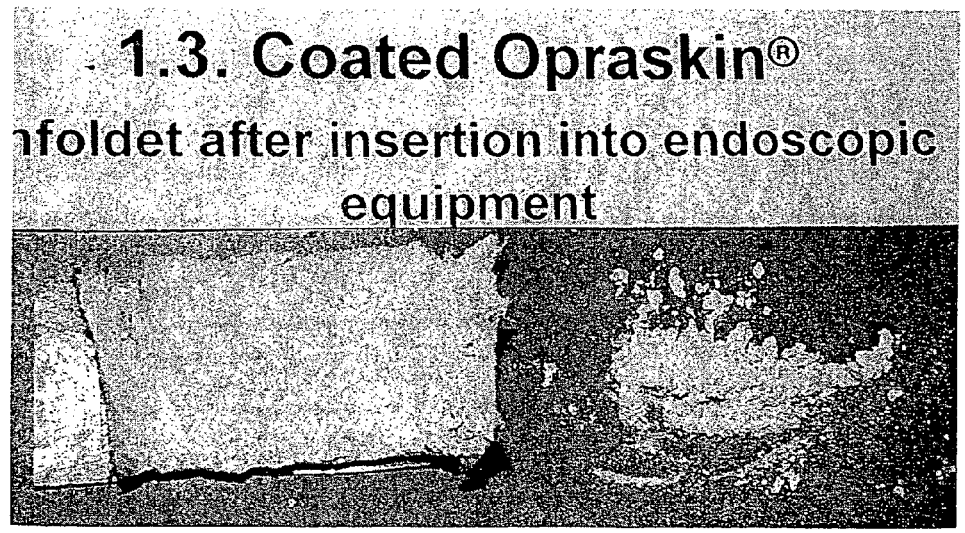
Figure 2:
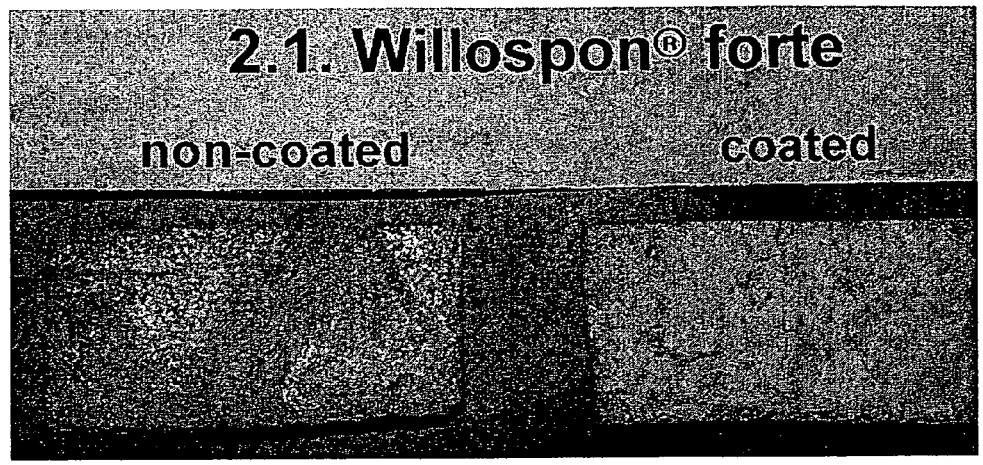
FIG. 2.1 illustrates Willospon® forte in both non-coated and coated states.
Figure 2:
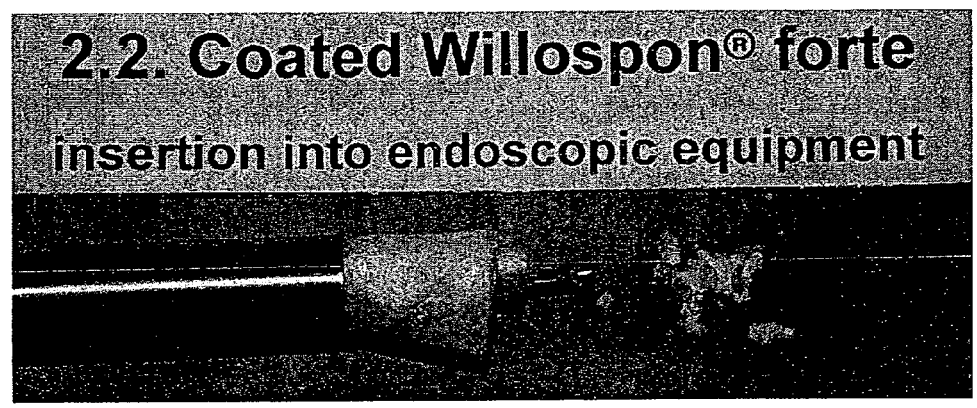
Figure 2:
Figure 3:
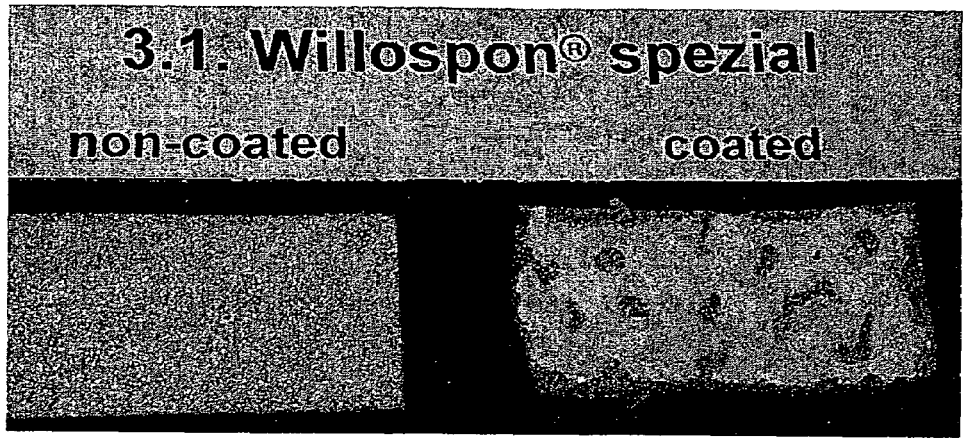
FIG. 3.1 illustrates Willospon® Spezial in both non-coated and coated states.
Figure 3:
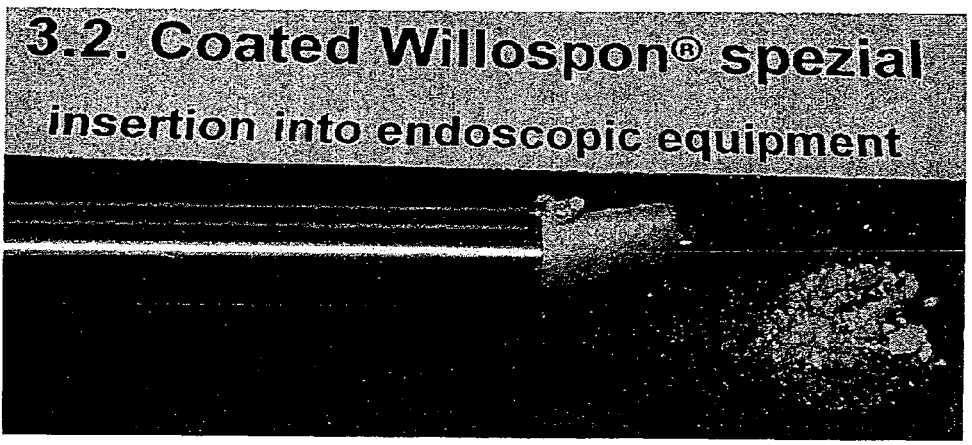
Figure 3:
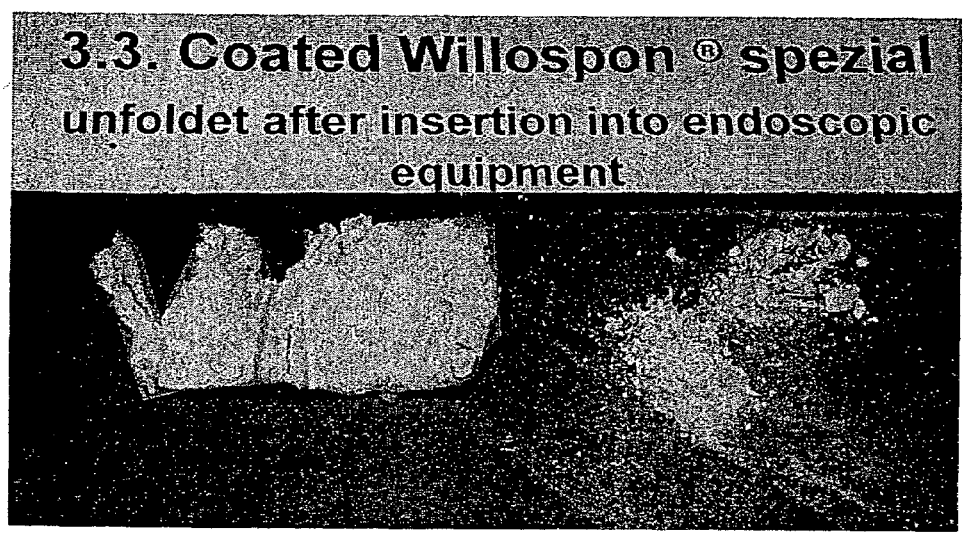
Figure 4:
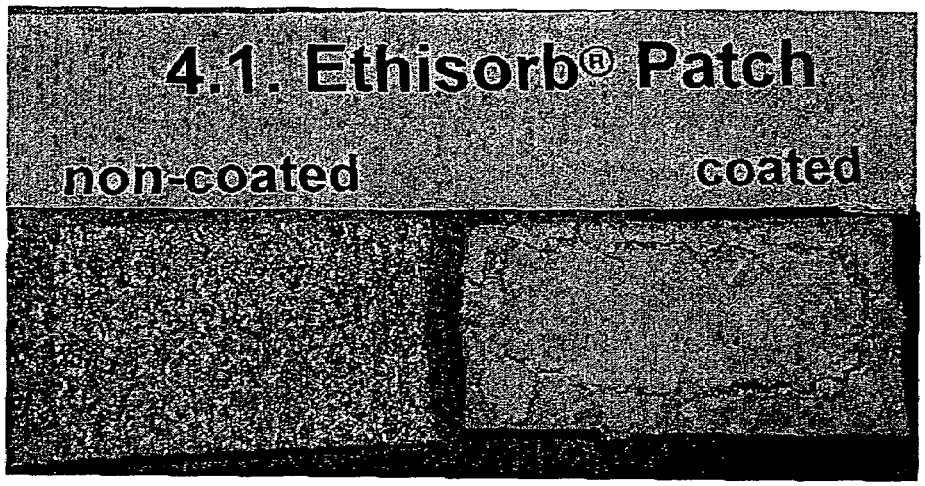
FIG. 4.1 illustrates an Ethisorb® Patch in both non-coated and coated states.
Figure 4:
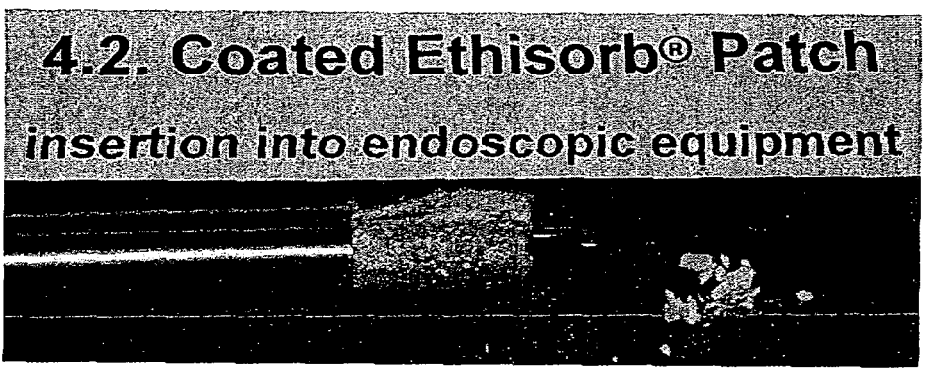
Figure 4:
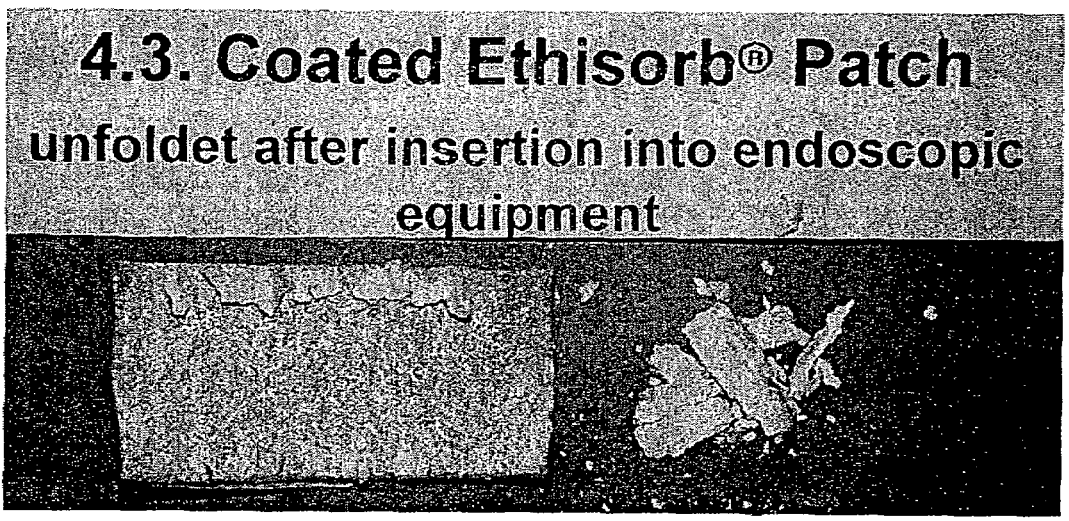
Figure 5:
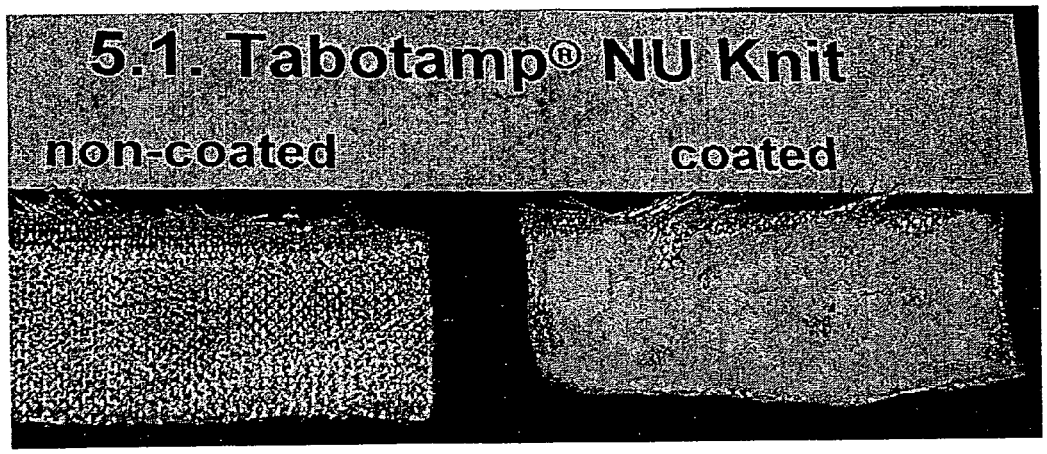
FIG. 5.1 illustrates Tabotamp® NU Knit in both non-coated and coated states.
Figure 5:
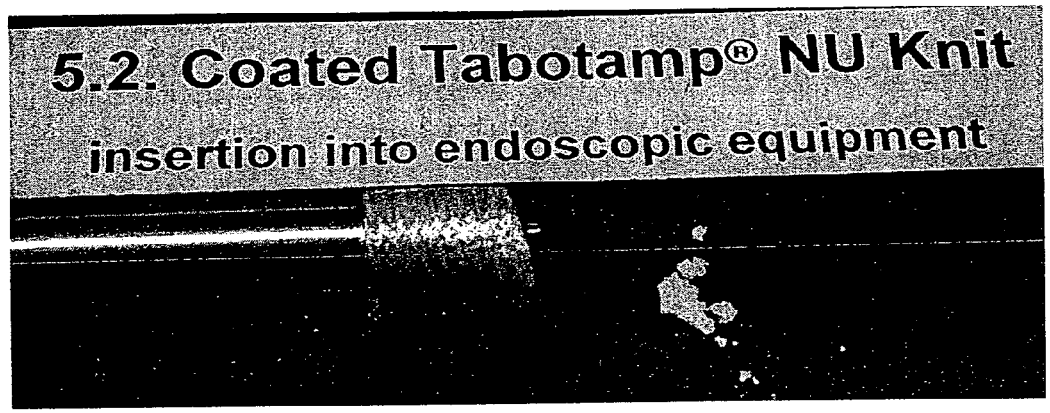
Figure 5:
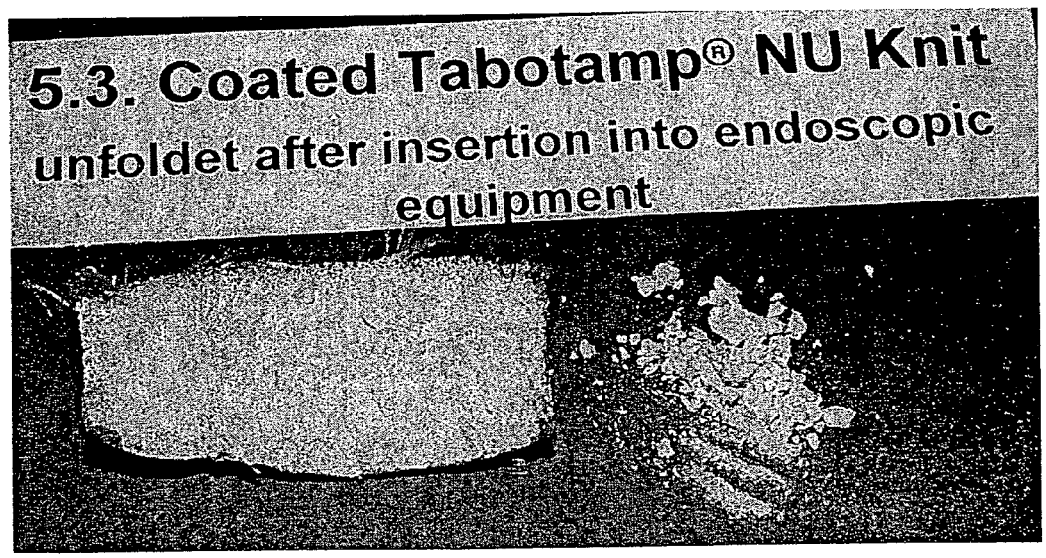
Figure 6:
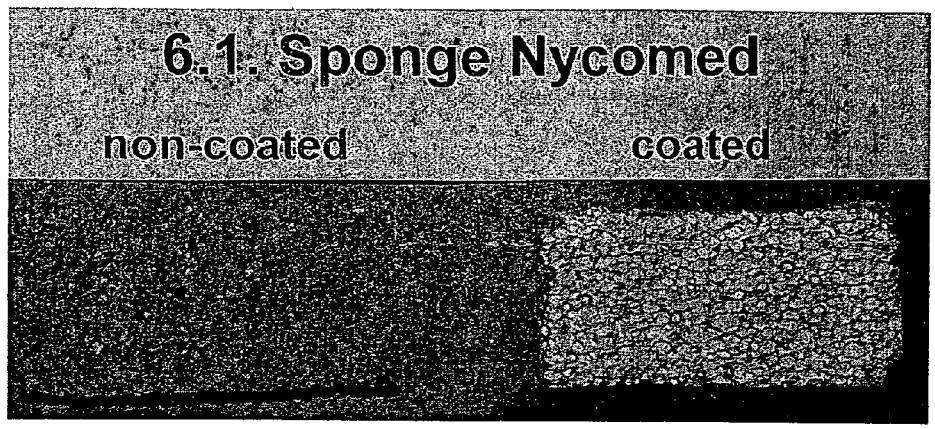
FIG. 6.1 illustrates Sponge Nycomed in both non-coated and coated states (lab sample)
Figure 6:
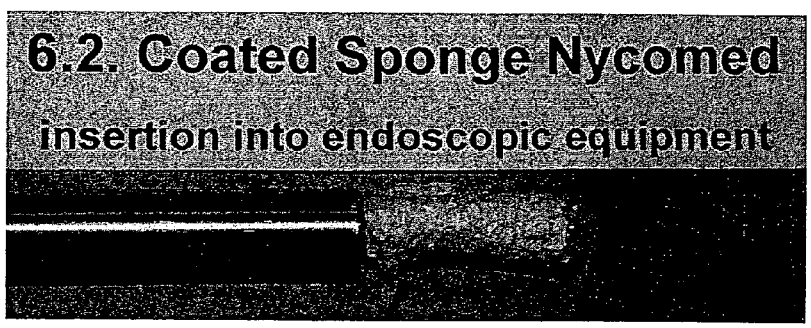
Figure 6:
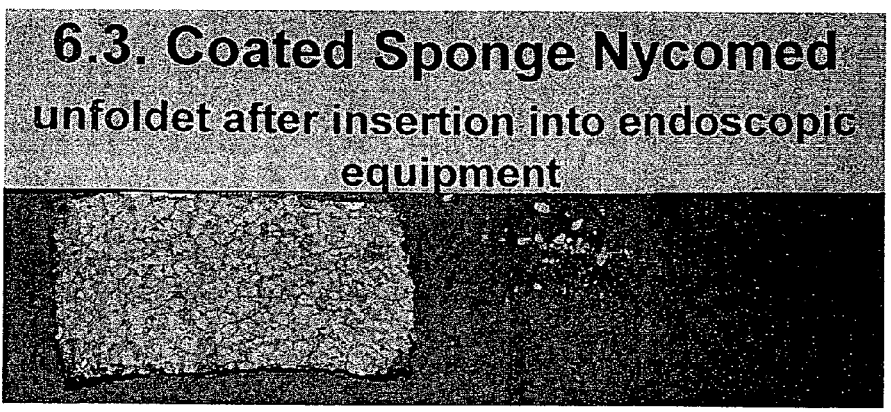
Figure 6:

Examples I-IV below illustrate various procedures for preparation of a coated collagen sponge with different fibrinogen and thrombin raw materials.

Fibrinogen Raw-Materials

|  | % of total substance | | |
| --- | --- | --- | --- |
| Component | Formulation A | Formulation B | Formulation C |
| Human fibrinogen | 36-52 | 42-47 | 36-52 |
| Human albumin | 16-24 | 20-24 | 16-24 |
| Total protein | 52-76 | 62-71 | 52-76 |
| Sodium chloride | 8-14 | 0 | 8-14 |
| tri Sodium citrate | 2-4 | 1-3 | 2-4 |
| Arginine (hydrochloride) | 15-26 | 15-21 | 15-26 |
| Glycine | 0 | 6-9 | 1-2 |
| Histidine | 0 | 3-5 | 0 |
| Sucrose | 0 | 0 | 1-2 |
| Residual moisture | <=2 | 2-4 | <=1.5 |

Thrombin Raw-Materials

| Formulation | Activity (I.U/mg substance) | Residual moisture | additional substances additives |
| --- | --- | --- | --- |
| Human thrombin A | 360-540 | <=3% | Human albumin, sodium chloride, sodium citrate |
| Human thrombin B | 7-10 | <=3% | Human albumin, sodium chloride, sodium citrate |
| Human thrombin C | 35-60 | <=3% | Human albumin, sodium chloride, sodium acetate, glycine |

Example I

In the present example, the suspension contains human fibrinogen formulation B and human thrombin formulation B.

A final suspension volume of 3500 ml was obtained by applying the following quantities and parameters:

Fibrinogen mixture:

2800 ml ethanol (94% at 2° C.-8° C.)

492.5 g human fibrinogen formulation B 493.5 mg riboflavin

The fibrinogen mixture was stored for 8-16 hours at 2-8° C. while being stirred.

Thrombin Mixture:

100 ml ethanol (100% at −30° C.)

12.27 g human thrombin formulation B

The thrombin mixture was stored for 8-16 hours at −30° C.

Suspension:

157 ml of thrombin mixture is added to the fibrinogen mixture.

A 94% ethanol at 2-8° C. was added to fill to the final suspension volume of 3500 ml.

Suspension Characteristics:
1. Ethanol concentration: 94.3%
2. Sedimentation behaviour:
a) sedimentation volume 5 minutes after start: 98% of test volume,
b) sedimentation volume 24 hours after start: 64% of test volume.
3. Particle size (Folk Ward mean diameter): 56.4+/−1.3 µm Carriers in the form of collagen strips were coated with the suspension. First, 48 collagen sponge strips were pre-incubated in a cooling chamber, at the following conditions:
Temperature: 5.2° C.
Absolute humidity: 4.8 g water per kg air
Incubation time: 18.5 hours The coated collagen sponge strips were dried as follows:
The coated strips were incubated for 15 minutes at a temperature of 5.2° C. and an absolute humidity of 4.8 g water per kg air.

The coated strips were then dried in a vacuum drying chamber at the following drying conditions:
Air condition: temperature of 5.2° C., absolute humidity of 4.8 g water per kg air
Air flow through aspiration valve: 23 m³ per hour
Vacuum: 59 mbar
Drying time: 4 hours The abrasion of the obtained coating on the collagen sponge strips was approximately 0.2 mg/cm² when shaken on a Vibrofix shaker at a frequency of 800-1200 rpm for 2 minutes.

Example II

In the present example, the suspension contains human fibrinogen formulation C and human thrombin formulation C.

A final suspension volume of 3500 ml was obtained by applying the following quantities and parameters:
Fibrinogen Mixture:
2252 ml ethanol (94% at 2° C.-8° C.)
370.7 g human fibrinogen formulation C
493.5 mg riboflavin The fibrinogen mixture was stored for 8-16 hours at 2-8° C. while being stirred.
Thrombin Mixture:
188 ml ethanol (100% at −30° C.)
12 vials human thrombin formulation C (10650 I.U./vial)/12 ml water for injection The thrombin mixture was stored for 8-16 hours at −30° C.
Suspension:
164.5 ml of thrombin mixture were added to the fibrinogen mixture.
A 94% ethanol at 2-8° C. was added to fill to the final suspension volume of 3500 ml.

Suspension Characteristics:
1. Ethanol concentration: 94.1%
2. Sedimentation behaviour:
a) sedimentation volume 5 minutes after start: 94% of test volume,
b) sedimentation volume 24 hours after start: 71% of test volume.
3. Particle size (Folk Ward mean diameter): 49.2+/−0.93 µm Carriers in the form of collagen strips were coated with the suspension. First, 48 collagen sponge strips were pre-incubated in a cooling chamber, at the following conditions:
Temperature: 4.8° C.
Relative humidity: 90.3%
Incubation time: 22.25 hours The coated collagen sponge strips were dried as follows:
The coated strips were incubated for 13 minutes at a temperature of 4.9° C. and an absolute humidity of 4.8 g water per kg air.

The coated strips were then dried in a vacuum drying chamber at the following drying conditions:
Air condition: temperature of 5.2° C., absolute humidity of 4.9 g water per kg air
Air flow through aspiration valve: 25 m³ per hour
Vacuum: 60 mbar
Drying time: 4 hours The abrasion of the obtained coating on the collagen sponge strips was approximately 0.3 mg/cm² when shaken on a Vibrofix shaker at a frequency of 800-1200 rpm for 2 minutes

Example III

In the present example, the suspension contains human fibrinogen formulation C and human thrombin formulation C.

A final suspension volume of 780 ml was obtained method by applying the following quantities and parameters:
Fibrinogen Mixture:
700 ml ethanol (94% at 2° C.-8° C.)
84.42 g human fibrinogen formulation C
110 mg riboflavin The fibrinogen mixture was stored for 8-16 hours at 2-8° C. while being stirred.
Thrombin mixture:
35 ml ethanol (100% at −30° C.)
0.54 g human thrombin formulation C The thrombin mixture was stored for 8-16 hours at −30° C.
Suspension:
23.0 ml of thrombin mixture was added to the fibrinogen mixture.
A 100% ethanol at 2-8° C. was added to fill to the final suspension volume of 780 ml.

Suspension Characteristics:
1. Ethanol concentration: 94%
2. Sedimentation behaviour:
a) sedimentation volume 5 minutes after start: 92% of test volume,
b) sedimentation volume 24 hours after start: 72% of test volume.
3. Particle size (Folk Ward mean diameter): 60.5+/−0.5 µm Carriers in the form of collagen strips were coated with the suspension. First, 8 collagen sponge strips were pre-incubated in a cooling chamber, at the following conditions:
Temperature: 6.0° C.
Relative humidity: 85%
Incubation time: 18.5 hours The coated collagen sponge strips were dried as follows:
The coated strips were incubated for 45 minutes at a temperature of 5° C. and a relative humidity of 85%.

The coated strips were then dried in a vacuum drying chamber at the following drying conditions:
Air condition: temperature of 5° C., relative humidity 85%
Air flow through aspiration valve: 1.2 m³ per hour
Vacuum: 35 mbar
Drying time: 4 hours The abrasion of the obtained coating on the collagen sponge strips was approximately 0.3 mg/cm$^2$ when shaken on a Vibrofix shaker at a frequency of 800-1200 rpm for 2 minutes.

Example IV

In the present example, the suspension contains human fibrinogen formulation A and human thrombin formulation A.

A final suspension volume of 3120 ml was obtained by applying the following quantities and parameters:

Fibrinogen Mixture:
2540 ml ethanol (100% at 2° C.-8° C.)
311.6 g human fibrinogen formulation A
440 mg riboflavin
The fibrinogen mixture was stored for 8-16 hours at 2-8° C. while being stirred.

Thrombin Mixture:
210 ml ethanol (100% at −30° C.)
229 g human thrombin formulation A Suspension:
87.3 ml water for injection were added to the fibrinogen mixture.
The thrombin mixture was added to the fibrinogen mixture.
A 100% ethanol at 2-8° C. was added to fill to the final suspension volume.

Suspension Characteristics:
1. Ethanol concentration: 97%
2. Sedimentation behaviour:
a) sedimentation volume 5 minutes after start: 95.6% of test volume,
b) sedimentation volume 24 hours after start: 63.5% of test volume.
3. Particle size (Folk Ward mean diameter): 51.8+/−0.8 µm Carriers in the form of collagen strips were coated with the suspension. First, 48 collagen sponge strips were pre-incubated in a cooling chamber, at the following conditions:
Temperature: 6.5° C.
Relative humidity: 90%
Incubation time: 22.5 hours The coated collagen sponge strips were dried as follows:
The coated strips were incubated for 10 minutes at a temperature of 6.5° C. and a relative humidity of 90%.
The coated strips were then dried in a vacuum drying chamber at the following drying conditions:
Air condition: temperature of 6.5° C., relative humidity 90%
Air flow through aspiration valve: 21 m$^3$ per hour
Vacuum: 58 mbar
Drying time: 4 hours The abrasion of the obtained coating on the collagen sponge strips was less than 0.1 mg/cm$^2$ when shaken on a Vibrofix shaker at a frequency of 800-1200 rpm for 2 minutes.

Example 1

Aprotinin as a Component of TachoComb®

In Vitro Investigation of the Anti-Fibrinolytic Activity Under Wash-Out Conditions Similar to an In Vivo Situation The aim of the present investigation was to show the efficacy of aprotinin as a component of TachoComb H under hyperfibrinolytic conditions by using in vitro test models.

TachoComb S is an off-white, coated, sponge-like patch. The patch of foamed dry collagen is used as carrier of the active, solid components. The size of the patch is 9.5×4.8×0.5 cm. The active side is colored yellow. 1 cm$^2$ TachoComb S patch (thickness 0.5 cm) consists of:

| | |
|---|---|
| Collagen of equine origin coated with: | 2.1 mg |
| human fibrinogen | 5.5 mg |
| human thrombin | 2.0 I.U. |
| riboflavin (yellow color as marker of coated area) | 16.5 µg |

Experimental in vivo dose-finding tests have confirmed that the above concentrations of thrombin and fibrinogen result in maximum adhesive strength (see Example 3).

TachoComb H containing human thrombin, human fibrinogen and aprotinin was compared to TachoComb S containing only human thrombin and human fibrinogen as active components.

Two test models were developed for a quantitative determination of efficacy under hyper-fibrinolytic conditions which could be considered to be relevant for surgical conditions and which allowed to perform the number of tests necessary for demonstrating a significant effect.

In test model 1 the test sample was applied to a synthetic fabric as adhesion surface. A defined hole had been cut into the fabric to simulate e.g. the perforation of a blood vessel.

The sealing was exposed to two different fibrinolytic solutions (incubation solutions) through the hole. One of these solutions additionally contained the antifibrinolytic component $\alpha_2$-antiplasmin.

Composition of the Incubation Solutions:
All substances are diluted in buffer 1: 50 mM Trometamol, 100 mM NaCl, 2.5 mM CaCl$_2$, 2 mg/ml BSA (protease free), 0.5 mg/ml Na-azid/ml Incubation solution I (1 µmolar plasminogen, 1 nmolar tissue plasminogen activator (tPA), 1 µmolar $\alpha_2$-antiplasmin) 49 µl buffer 1, pH 7.4
51 µl plasminogen solution (conc. 4.9 µmolar Coachrom human plasminogen activity)
50 µl tPA solution (50 nmolar)
100 µl $\alpha_2$-antiplasmin solution (2.5 µmolar)

Incubation solution II (1 µmolar plasminogen, 1 nmolar tissue plasminogen activator) 149 µl buffer1, pH 7.4 51 µl plasminogen solution (conc. 4.9 µmolar Coachrom human plasminogen activity)
50 µl tPA solution (50 nmolar)

The incubation solution was replaced in 2-hour-periods to simulate a wash-out effect. At that occasion the adhesion was controlled. A pressure of 50 mbar was laid on the sample. The time when the sample detached at a pressure of ≦50 mbar was registered.

Test model 2 was to demonstrate the fibrinolytic effect of damaged intestine tissue. The test sample was applied to pig intestine (ex vivo) as adhesion surface. A defined perforation had been cut into the intestine to enable the incubation solution to come into contact with the fibrin clot and simulate a wash-out effect. The incubation solution was changed at registered times and at that moment pressure of 50 mbar was laid on the sample. The time when the sample detached at a pressure of ≦50 mbar was registered.

The results revealed considerable differences between TachoComb H containing aprotinin and TachoComb S without aprotinin.

In test model 1 using the incubation solution containing tissue plasminogen activator, plaminogen and $\alpha_2$-antiplasmin the fibrinolysis time for TachoComb H was 41.2±7.3 hours compared to 12.8±2.8 hours for TachoComb S.

In test model 1 using the incubation solution containing only tissue plasminogen activator and plasminogen the fibrinolysis time for TachoComb H was 31.6±5.3 hours compared to 8.3±1.8 hours for TachoComb S.

In test model 2 the detachment time for TachoComb H was 78.4±16.3 hours compared to 6.5±1.8 hours for TachoComb S.

A lot of fibrin could still be observed on the test sample. But the sample detached under pressure from the intestine surface because the strength of adhesion between fibrin clot and intestine surface became weaker.

In both models the antifibrinolytic effect of aprotinin as an active component in TachoComb H could be demonstrated very clearly.

In test model 1 the prolongation of the fibrinolysis time due to aprotinin as an active component of TachoComb H was 320% for incubation solution I containing $\alpha_2$-antiplasmin and 380% for incubation solution II without $\alpha_2$-antiplasmin.

Test model 1 also showed the additional antifibrinolytic effect of $\alpha_2$-antiplasmin by prolongation of fibrinolysis time for TachoComb H from 31.6 to 41.2 hours (130%) and for TachoComb S from 8.3 to 12.8 hours (154%).

Example 2

Comparison of Coated Nycomed Sponge (TachoComb S) with Other Carrier Products Coated Identically as TachoComb S.

Adhesion of the Layer

Procedure
1. Coating of different carriers

| Brand name | Material | Manufactured/Distributed by |
|---|---|---|
| Opraskin ® | Collagen sponge | Lohmann, Postfach 2343, D-56513 Neuwied |
| Willospon ® forte | Collagen sponge (calves) | Will-Pharma, Postbus 30, NL 1160 AA Zwanenburg |
| Willospon ® Special | Gelatine sponge | Will-Pharma, Postbus 30, NL 1160 AA Zwanenburg |
| Ethisorb ® Patch | Polyglactin910/ Polydioxanon | Johnson/Johnson (manufacturer) Ethicon, Robert-Koch-Str. 1 D-22851 Norderstedt |
| Tabotamp ® NU Knit | Oxidized regenerated cellulose | Johnson/Johnson (manufacturer) Ethicon, Robert-Koch-Str. 1 D-22851 Norderstedt |
| Collagen sponge Nycomed | Equine collagen sponge | Nycomed Austria Sankt-Peter-Str. 25 A-4021 LINZ |

An area of 2×4, 5 cm$^2$ of each carrier was coated with TachoComb S coating suspension. The amount of coating suspension corresponded to TachoComb specification (5,5 mg fibrinogen/cm$^2$). The samples were dried.
2. A sample of 1×4 cm$^2$ was prepared of each coated carrier.
3. The adhesion of the layer was tested as follows Method Description Apparatus
Analytical balance (measurement precision±0.5 mg)
Vibrofix shaker combined with fixation device
Ruler with millimeter graduation
Stop-watch, scalpel, tubes of 2 cm internal diameter with stopper Procedure
4×1 cm$^2$ coated area are cut out of the coated carrier using a scalpel.

The sample is placed in a balanced tube with stopper. Then it is shaken on the Vibrofix shaker (frequency: about 1000 rpm) for 2 min.

The sheet is removed and the residual quantity of coating material (abrasion: mg/cm$^2$) is reweighed.

Calculation:

$$\text{Abrasion (mg/cm}^2\text{)} = \frac{\text{weight of residual (mg)} - \text{tare (mg)}}{4 \text{ cm}^2}$$

Results

| Carrier | Substance | Abrasion (mg/cm$^2$) |
|---|---|---|
| Opraskin ® | lyoph. Collagen | 2.1 |
| Willospon ® forte (3 mm) | lyoph. Collagen | 1.2 |
| Willospon ® Spezial (1 mm) | Gelatine | 2.1 |
| Ethisorb ® Patch (ZVP609) | Polyglactin/dioxanon | 14.3 |
| Tabotamp ® NU Knit | oxidized cellulose | 9.2 |
| Collagen sponge Nycomed | collagen, foamed | 0.15 |

Comment

All carriers except Nycomed collagen sponge are not flexible after coating.

The sample has to be cut out very cautiously. If it is cut out by using a pair of scissors a lot of the coating material will flake off because the layer in itself is rigid. Ethisorb® patch showed almost no connection with the coating material at all. When shaken a little bit, all of the coating peels off like a "carpet".

The difference between Nycomed collagen sponge and the other carrier materials shows quite clearly.

Elasticity of the Moistened Coated Carrier

Procedure
1. Coating of different carriers
An area of 2×4.5 cm$^2$ of each carrier was coated with TachoComb S coating suspension.

The amount of coating suspension corresponded to TachoComb specification (5.5 mg fibrinogen/cm$^2$). The samples were dried.

2. A sample of about 5-7 cm$^2$ was prepared of each coated carrier. The exact starting area of the dry sample was determined.

3. The sample was moistened and put on an elastic Latex sheet fixed to a special equipment as described in detail under the heading "procedure". Then pressure was put on the Latex sheet which expanded. After 2 times of expansion and relaxation the sheet is expanded for a third time. The area of the carrier was measured at the highest expansion point.

Method Description

Apparatus/Chemicals
Peristaltic pump (IKA PA-SF)
Pressure buffering bottle (3 outlets)
VDO manometer (0-250 mbar)

Glass funnel (Ø opening1: 30 mm, opening 2:15 mm)
Silicone tubings and clamps, Latex gloves (Semper med), scalpel, ruler with millimeter graduation, scissors
Physiological saline Procedure The following equipment is connected air tight to the three outlets of the pressure buffering bottle via silicone tubings:
a) peristaltic pump
b) manometer
c) glass funnel/opening 2

A double sheet of about 8×8 cm² is cut from a Latex glove. This sheet is fixed airtight to the glass funnel/opening 1.

About 5-7 cm² coated area are cut out of the coated carrier using a scalpel.

The area of the sample is measured (starting area). The coating of the sample is moistened with saline and placed on the Latex sheet. Then it is pressed to the Latex sheet manually for about 1 min.

Using the peristaltic pump the Latex sheet is expanded by putting on a pressure of about 70 mbar. This is repeated twice with relaxation of the Latex sheet afterwards. At the third expansion the area (length and width) of the coated carrier is measured at the highest point of Latex sheet expansion.

Calculation:

$$\text{"Elasticity" factor} = \frac{\text{area of the carrier at third expansion}}{\text{starting area of sample}}$$

Results

| Carrier | Substance | Elasticity factor |
| --- | --- | --- |
| Opraskin ® | lyoph. collagen | 1.78 |
| Willospon ® forte (3 mm) | lyoph. collagen | 1.53 |
| Willospon ® Spezial (1 mm) | gelatine | 1.79 |
| Ethisorb ® Patch (ZVP609) | Polyglactin/dioxanon | 1.0 |
| Tabotamp ® NU Knit | oxidized cellulose | 1.15 |
| Collagen sponge Nycomed | collagen, foamed | 1.55 |

Comment:

The elasticity of the moistened Collagen sponge Nycomed (TachoComb S) is one of the important characteristics of the product. Elasticity is essential in thoracic and abdominal surgery. After gluing the carrier should be able to follow for example expansion and relaxation movements of the lungs or intestines. Especially Ethisorb® showed no elasticity at all. It detached from the coating immediately. Coated Willospon® Spezial and Opraskin® showed structural defects during the test.

Use of Coated Carrier in Endoscopic Surgery

Procedure:

1. Coating of different carriers

An area of 2×4 cm² of each carrier was coated with TachoComb S coating suspension. The amount of coating suspension corresponded to TachoComb specification (5.5 mg fibrinogen/cm²). The samples were dried.

2. The handling of the coated carrier samples for use in endoscopic surgery and the loss of coating due to this handling are documented by a digital photo-equipment.

Method Description

Apparatus

Figure 7:
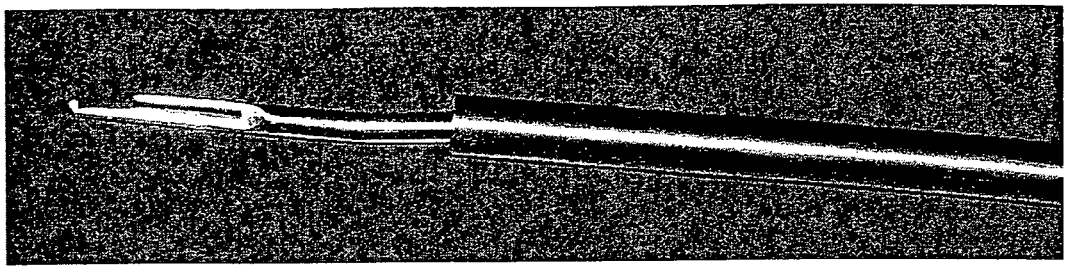
FIG. 7, in each of its three illustrations, shows an endoscopic tool Endodock®.
Figure 7:
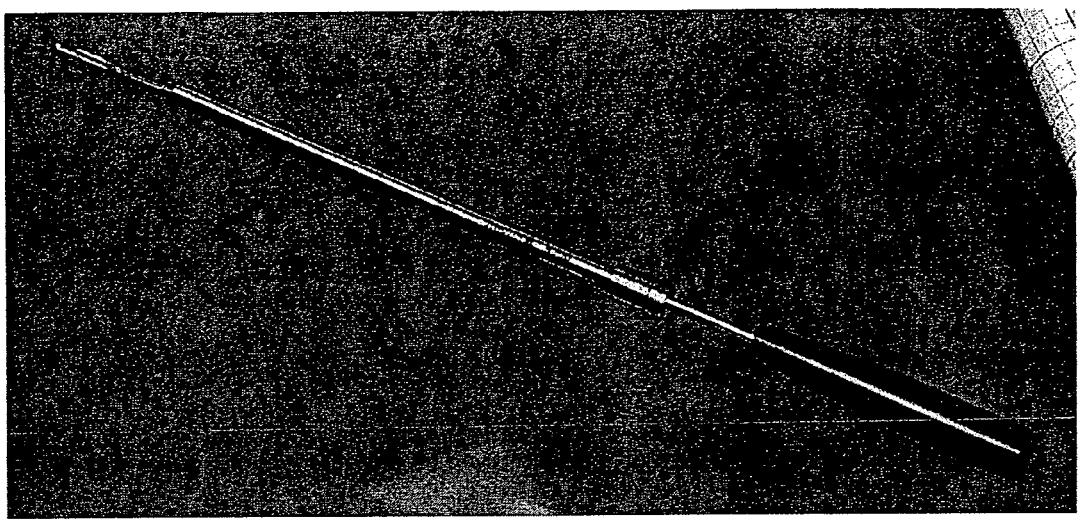
Figure 7:
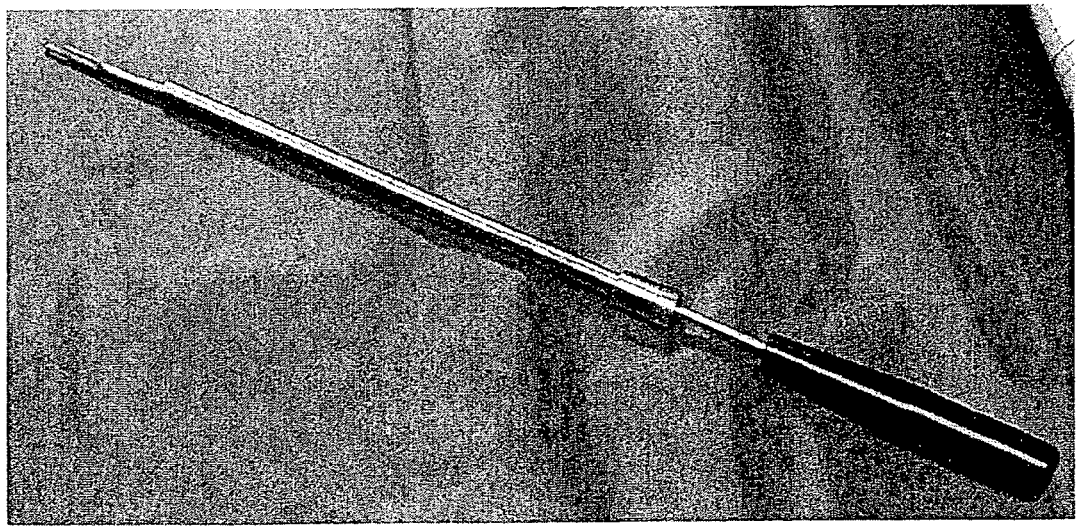
Figure 8:
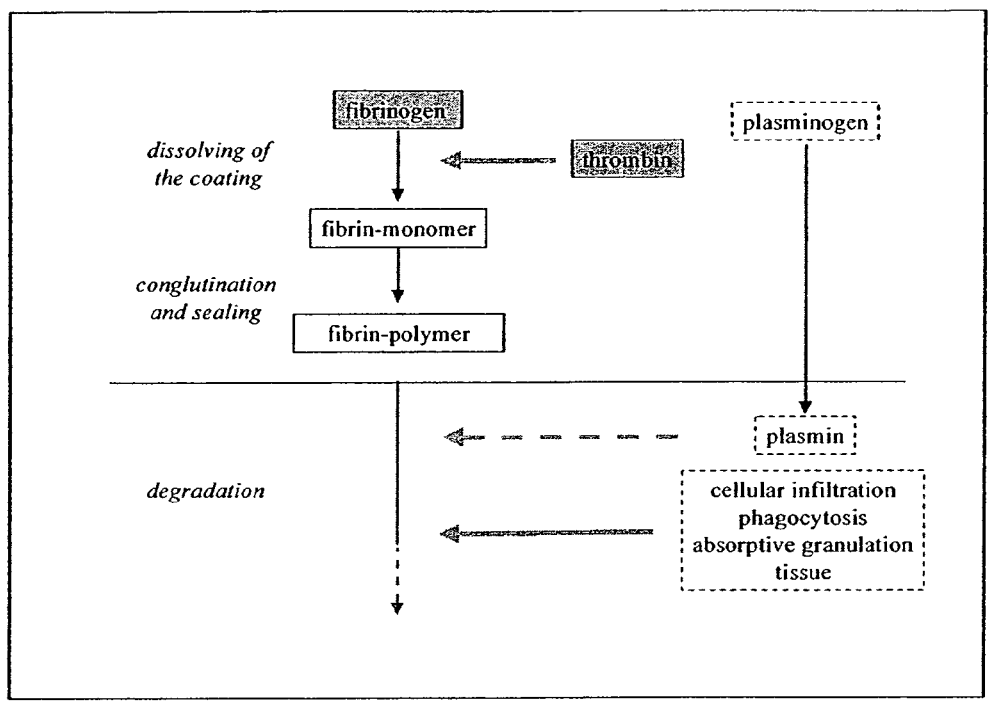
FIG. 8 is a diagram illustrating blood coagulation and degradation of clot and carrier patch; the active components of the carrier coating are shown in grey shaded boxes.

Endodock: Endoscopic tool designed for the use of TachoComb® in endoscopic surgery (see FIG. 7). Digital photo-equipment.

List of Investigated Carriers

| Carrier | Carrier material |
| --- | --- |
| Opraskin ® | lyoph. collagen |
| Willospon ® forte (3 mm) | lyoph. collagen |
| Willospon ® Spezial (1 mm) | gelatine |
| Ethisorb ® Patch (ZVP609) | Polyglactin/dioxanon |
| Tabotamp ® NU Knit | oxidized cellulose |
| Collagen sponge Nycomed | collagen, foamed |

Procedure

Picture series taken of each carrier:

1. Picture: Documentation of the non-coated and coated carrier samples.

2. Picture: The coated samples are inserted into the endoscopic equipment (Endodock).

The sample has to be flattened manually to be able to wrap it around a guiding "pin". Then the sample is inserted carefully into the steel tube of 10 mm in diameter.

Documentation of the sample partially inserted into the Endodock tube.

3. Picture: The sample is pushed out carefully. Afterwards the sample has to be unfolded.

The coating that has split of the carrier due to this handling is gathered beside the carrier.

The unfolded sample after insertion into the endoscopic equipment and the loss of the coating due to this handling are documented.

Comment

TachoComb S (coated equine collagen sponge/Nycomed) in endoscopic surgery is the most demanding application of the product. TachoComb S is inserted into an endoscopic equipment. The tube of this equipment is generally 10-13 mm in diameter. To be inserted into the tube TachoComb S is flattened and then wrapped around a guiding "pin" and then inserted carefully into the tube. Therefore the connection of the coating to the carrier and within itself has to be strong but the product has to stay flexible enough in dry condition to be bent and rolled up. When brought to the site of the surgery TachoComb S is carefully pulled out of the tube. Then it has to be unwrapped and placed to the wound surface. This often requires some adjustments. Therefore adhesion of the layer to the carrier should be strong enough to withstand this handling.

Results

The results are seen from the enclosed FIGS. 1-6. An estimate of the cast of coating material is as follows:

| | |
|---|---|
| Opraskin ® | 30-40% |
| Willospon ® forte | 60-70% |
| Willospon ® Spezial | 50% |
| Tacotamp ® NU knit | 60-70% |
| Ethisorb ® Patch | 95% |
| Collagen sponge Nycomed | <5% |

As Ethisorb ® is a very rigid carrier the adhesion of the coating is very bad. Therefore coated Ethisorb ® lost almost all of the coating in this investigation. Compared to coated collagen sponge of Nycomed all the other investigated carriershave a flat surface to be coated. Therefore the coating lies like a "flat carpet" on the carrier. This leads to a rather unflexible structure of the dry coated carriers. Bending or rolling up often breaks the coating in itself.

After insertion of the coated carriers into the tube of the endoscopic equipment and the unfolding of the sample afterwards all carriers except collagen sponge of Nycomed lost quite a lot of the coating so that large areas are left without coating material.

The structure and texture of Nycomed collagen sponge is the basis of the high flexibility of TachoComb S in dry or moistened conditions. Nycomed collagen sponge is foamed and has polygonal chambers inside. On the surface these chambers are cut to caverns. These caverns enlarge the coating surface. During coating the coating suspension is distributed evenly onto the structured surface. During the drying the solution containing both fibrinogen and thrombin is fixed as solids into the caverns. Therefore TachoComb S can be cut to desired sizes and can be inserted into endoscopic equipment with only a small loss of coating material or no loss at all.

The high flexibility of dry TachoComb S is a big advantage compared to all other investigated coated carriers.

Example 3

Dose-Finding Tests of Active Components

The dose of active components has been found by two different experimental models in which the strength of adhesion was measured: tensile strength on rat liver, adhesion strength against elevated tissue pressure in rat kidney.

A. Tensile Strength on Rat Liver

A wound of 1×1 cm and about 1 mm deep was made on the left lobe of liver of anesthetized rats in order to produce an oozing hemorrhage. The wound was sealed with a 1×1 cm piece of TachoComb S which was connected to a spring balance. The tension at which TachoComb S was torn off was measured.

B. Strength of Adhesion Against Elevated Tissue Pressure in Rat Kidney

A smooth level strongly bleeding wound was produced on the left kidney of anesthetized rats by cutting off about one quarter of its mass. The wound was sealed with TachoComb S test sheets. Tissue pressure was elevated by closing the venous drainage and pumping an isotonic citrate salt solution (pH 7.2) into the kidney. The pressure at which TachoComb S started to detach was measured.

TABLE 1

Strength of adhesion of TachoComb S containing different amounts of fibrinogen.

| Composition of the layer | | Tensile strength on | Strength of adhesion (mean ± SD) |
|---|---|---|---|
| | | | Strength of adhesion against elevated tissue pressure in |
| | | Tensile strength on | tissue pressure in |
| Fibrinogen, mg/cm$^2$ | Thrombin, IU/cm$^2$ | rat liver, N/cm$^2$ n = 5 | rat kidney, mbar n = 5 |
| 0 | 0 | 0.20 ± 0.02 | 47 ± 9 |
| 0 | 2.40 | 0.20 ± 0.03 | 63 ± 16 |
| 1.30 | 1.73 | 0.30 ± 0.06 | 81 ± 12 |
| 2.92 | 1.85 | 0.39 ± 0.05 | 101 ± 13 |
| 5.10 | 1.87 | 0.39 ± 0.03 | 110 ± 13 |
| 7.22 | 1.82 | 0.38 ± 0.02 | 97 ± 13 |
| 10.02 | 1.75 | 0.40 ± 0.07 | 87 ± 10 |

TABLE 2

Strength of adhesion of TachoComb S containing different amounts of thrombin.

| Composition of the layer | | Tensile strength on | Strength of adhesion (mean ± SD) |
|---|---|---|---|
| | | | Strength of adhesion against elevated tissue pressure in |
| Fibrinogen, mg/cm$^2$ | Thrombin, IU/cm$^2$ | rat liver, N/cm$^2$ n = 5 | rat kidney, mbar n = 5 |
| 0 | 0 | 0.20 ± 0.02 | 47 ± 9 |
| 6.15 | 0 | 0.27 ± 0.01 | 57 ± 10 |
| 4.72 | 0.92 | 0.39 ± 0.02 | 84 ± 9 |
| 5.10 | 1.87 | 0.39 ± 0.03 | 110 ± 13 |
| 4.78 | 4.95 | 0.35 ± 0.02 | 97 ± 9 |
| 4.70 | 9.63 | 0.30 ± 0.02 | 109 ± 13 |
| 4.75 | 19.83 | 0.27 ± 0.03 | 91 ± 20 |

The obtained results revealed considerable differences between several variations. The optimal range for human thrombin was 0.9 to 10 I.U./cm$^2$ with a constant human fibrinogen content of about 5 mg/cm$^2$. The optimal range for human fibrinogen was 2.9 to 7.2 mg/cm$^2$ with a constant human thrombin content of about 2 I.U./cm$^2$ These in vivo tests confirmed that both the concentration of fibrinogen (4.3-6.7 mg/cm$^2$) and the concentration of thrombin (1.5-2.5 IU/cm$^2$), which are used in other TachoComb formulations (TachoComb® and TachoComb H) also result in maximal adhesive strength for TachoComb S.

Example 4

Efficacy of TachoComb S in Sealing Spleen and Liver Lesions in Dogs

The aim of this investigation was to compare the hemostatic efficacy of TachoComb H (containing aprotinin) with TachoComb S (without aprotinin) in a canine model of spleen and liver lesions. Incision and puncture (0.5 cm depth) of the spleen were chosen to mimic oozing hemorrhage. Resection of the tip of the cranial liver lobe was performed to mimic a strongly bleeding surface wound (2 to 3 cm$^2$). A TachoComb H or TachoComb S patch was applied as the only means of hemostasis to the wounds (same batch used for spleen and liver lesion in the same dog). Necropsy was done 48 hours after surgery as this is the period with the highest risk of re-bleeding in clinical practice.

Complete hemostasis was achieved with both products. No case of secondary hemorrhage was observed at 48-hours necropsy neither at gross observation nor at histological examination.

Also histologically there were no differences between dogs applied TachoComb H or TachoComb S when evaluating splenic and hepatic lesions covered with the respective patches with regard to hemostasis and healing of the wound. No case of secondary hemorrhage was observed after surgery.

The data of the blood count revealed similar results for both treatment groups with a mild rise in white blood count 48 h post surgery. There were no differences between groups or between time concerning any of the other parameters evaluated. Also the coagulation tests revealed no differences related to the presence or absence of aprotinin. An elevation of blood fibrinogen content was evident in both treatment groups at 48 hours post surgery. The elevation of white blood count and blood fibrinogen content can be attributed to an inflammatory response to the surgical trauma and are not considered as toxic side effect of TachoComb H or S It is concluded that TachoComb S (without aprotinin) exerts the same efficacy as TachoComb H (containing aprotinin) in treatment of oozing and strongly bleeding parenchymal wounds in dogs. The stability of the clot under the chosen conditions was not influenced by the presence or absence of aprotinin.

Example 5

Comparative Hemostatic, Wound Sealing Effect and Resistance of Absorbable TachoComb S and TachoComb H: Experimental Study in the Pig Purpose for the Study The test was designed to assess the immediate efficacy and short term resistance of a hemostatic fleece on a spleen lesion induced in the pig.

Material and Methods 24 female pigs were used in the study. 2 groups of hemostatic fleeces were randomly tested: TachoComb H with aprotinin and TachoComb S without aprotinin.

On the day of surgery the animal received a fleece directly obturating a standardized 2×3 cm lesion surgically created on the ventral part of the spleen.

The immediate and hemostatic effect of the fleece was estimated, by counting the number of blisters and measuring the time necessary to stop haemorrhage. The adherence of TachoComb H and S was noted.

After 72 hours, the short term behavior and resistance of both materials was investigated by increasing the intrasplenic pressure (clamping of the venous vessels).

When the pressure reached an almost steady state, an adrenalin IV bolus (0.02 mg or 0.04 mg) was administered to increase arterial pressure, associated or not according to a Dobutamine chlorhydrate infusion.

By means of these pharmacological substances, the rupture of bleeding pressure of the TachoComb H and S repaired lesion was quoted for each animal.

Results

No difference was detected between treatments at the time of spleen lesion surgery on the hemostatic effect.

At the second look, after 72 hours, the macroscopic appearance of both fleeces was identical.

Acute pressure measurement and resistance to rupture were not significantly different between both experimental groups.

No rupture of the material occurred. Bleeding of the lesion was observed in 4 animals with TachoComb S and 2 animals with TachoComb H (with one additional blister in group 4).

Histological examination suggested that aprotinin may exert a protective effect on the fleece structure, aprotinin seemed to modify the microscopical pattern by lessening the degradation of the fleece. No specific cellular pattern was observed.

Conclusion

The immediate hemostatic activity of 2 formulations of TachoComb, S and H, was investigated in standardized spleen lesion model in 24 pigs.

Both materials behave similarly for efficacy, adherence to the lesion and compliance to the parenchyma. Their efficacy was impressive.

Their resistance to biodegradation and proteolysis was investigated at the $72^{nd}$ hour following surgery by increasing the intrasplenic pressure (by mechanical and pharmacological means) and the recording of the local resistance of the TachoComb H and S fleeces. No significant difference of the resistance of the 2 materials could be evidenced.

Histopathologic findings indicated however that the proteolytic degradation of TachoComb S was slightly more pronounced than for TachoComb H.

TachoComb S or TachoComb H were used as only means of hemostasis to seal strongly bleeding splenic lesions in pigs (surface lesion 2 cm×3 cm, 3-5 mm depth; n=12 per group). After 72 hours the intrasplenic pressure was increased by ligating the splenic vein(s). Thereafter intrasplenic pressure was additionally increased by injecting adrenaline. The pigs were observed for signs of rebleeding or occurrence of blood blisters under the patch. Histopathology of samples (lesion site sealed with TachoComb H and S) was performed after necropsy.

TachoComb S and TachoComb H exerted similar efficacy, adherence to the lesion and compliance to the parenchyma.

Example 6

Comparative Hemostatic Wound Sealing Effect and Resistance of Absorbable TachoComb S and TachoComb H: Experimental Study in the Pig in a Model of Acute Pancreatitis Purpose for the Study The test was designed to assess the immediate efficacy and short term resistance of a hemostatic fleece on a spleen lesion induced in the pig in a model of acute pancreatitis.

Materials and Methods 20 female pigs were used in the study. 2 groups of hemostatic fleeces were randomly tested: TachoComb H with aprotinin and TachoComb S without aprotinin.

On the day of surgery the animals received a fleece directly obturating a standardized 2×3 cm lesion surgically created on the ventral part of the spleen.

The immediate hemostatic effect of the fleece was evaluated, by counting the number of blisters and measuring the time necessary to stop hemorrhage. The adherence of TachoComb H and S was noted.

Then, using a sterile syringe, the gallblader was punctured, the bile was collected and 10 ml of bile were injected through the Wirsung's duct, to induce pancreatitis. Blood enzyme levels were monitored before and daily after surgery (lipase and amylase levels).

Small pieces of TachoComb H and S were deposited on the pancreas parenchyma on its gut connection.

After 72 hours, the short term behavior and resistance to enzymic degradation of TachoComb H and S were investigated by increasing the intrasplenic pressure (clamping of the venous vessels and pharmacological means).

When the pressure reached an almost steady state, an IV adrenalin bolus (0.02 mg or 0.04 mg) following a noradrenalin infusion of 0.02 to 0.04 mg/min was administered to increase arterial pressure, associated or not to a Dobutamine chlorhydrate perfusion of 0.3-0.6 mg/min.

By means of these pharmacological substances, the rupture of bleeding pressure of the TachoComb H and S repaired lesion was noted for each animal.

Results

On the spleen, both materials behave similarly for immediate hemostatic efficacy, adherence to the lesion and compliance to the parenchyma. Their efficacy was very impressive.

Both fleeces were unaltered by macroscopic examination, at day 3 although the enzymatic conditions were severe, especially on day 2 in the blood, and still on day 4 in the peritoneal fluid.

At the $72^{nd}$ hour, no significant difference of the resistance of both materials could be evidenced after increase of spleen pressure.

One rupture of the material occurred in the TachoComb S group. Bleeding of the lesion was observed in 1 animal with TachoComb S and 2 animals with TachoComb H (with one blister in the TachoComb H group).

Histopathologic findings indicated no significant difference in the degradation of TachoComb S compared to TachoComb H. No specific cellular pattern was observed on the spleen. Even on pancreatic samples, the pieces of TachoComb H and S in close contact with high concentration of pancreatic enzymes did not show any major change.

Conclusion

In conclusion, no clear difference appeared between TachoComb S and TachoComb H concerning their resistance to rupture in conditions of increased pancreatic enzymes environment.

No specific macroscopical nor microscopical evidence of modification of both TachoComb H and S fleeces could be detected.

The hemostatic efficacy of TachoComb S and TachoComb H was investigated in a standardized spleen lesion model (surface lesion 2 cm×3 cm, ca 3 mm depth; n=10/group) in pigs with acute pancreatitis induced by retrograde injection of bile in the Wirsung's duct and subsequent ligation of the pancreatic duct. Small pieces of TachoComb H and S were also applied on the pancreas at the site of pancreatic duct ligation. At 72 hours after surgery intrasplenic pressure was increased by ligating the splenic vein and i.v. adrenaline injection.

On the spleen TachoComb S and TachoComb H behaved similarly with regard to immediate hemostatic efficacy, adherence to the lesion and resistance to increased intrasplenic pressure despite marked increase of pancreatic enzyme levels (20-100 fold increase of amylase and lipase in blood and 10-100 fold increase of pancreatic enzymes in peritoneal fluid as compared to basal levels). Histopathologic findings indicated no significant difference in the degradation of TachoComb S and TachoComb H. No specific cellular pattern was observed on the spleen. Even on pancreatic samples following close contact of TachoComb H and S with high concentrations of pancreatic enzymes, the adherence of TachoComb H and S and histopathology did not reveal any major differences.

Thus, no specific macroscopical or microscopical difference between TachoComb S and TachoComb H appeared in this highly stressful model of acute pancreatitis in pigs.

Example 7

Comparative Brain Tissue Reaction and Effectiveness of Resorbable TachoComb H and TachoComb S: Experimental Study in a Rabbit Model Under Normal Coagulation and During Local Hyperfibrinolysis The aim of this study was to compare the efficacy of TachoComb S and TachoComb H following neurosurgical application. Brain lesions were induced in rabbits under normal coagulation conditions (brain tissue reaction=BTR, n=12 rabbits, eligible n=10) and under hyperfibrinolytic conditions (HF) by local r-tPA application (n=10 rabbits). Three cortical lesions were made per hemisphere (total of 6 lesions per animal; drilled brain lesion of 3 mm in depth and 4 mm in diameter).

The BTR Series

Two out of three lesions per hemisphere were treated with TachoComb H or TachoComb S respectively and one lesion per hemisphere was left empty as control. After sealing the lesions with TachoComb H or S bleeding time was measured under high magnification with continuous low flow irrigation with saline. After hemostasis was achieved in all lesions, arterial hypertension was induced by i.v. adrenaline injection (0.01 mg/kg adrenaline), thus increasing mean arterial pressure (MAP) to at least 120 mmHg. During this procedure observation for rebleeding continued. After lowering the MAP to normal values again the skin was closed. Time to necropsy was 3 and 7 days (n=5 rabbits each). In three animals magnetic resonance imaging was performed before necropsy on day 3. At necropsy a gross observation of the lesion sites was performed and samples for histopathology were taken.

The HF Series

After setting the lesions as described in the BTR series r-tPA was dropped onto the lesion (0.3 mg r-tPA in 0.5 ml saline per lesion) before all lesions were sealed alternatively with TachoComb S or TachoComb H. Bleeding time was measured under high magnification and continuos low irrigation with saline. Necropsy with gross observation took place on day 1 (n=7) and day 3 (n=3). Histopathology was performed on the specimens taken on day 3 for comparative reasons.

During the course of the entire study no differences between TachoComb S and TachoComb H were evident, neither with regard to sealing efficacy, tolerating increased MAP and duration of bleeding time, nor with regard to histopathology. Severe hemorrhage was evident in all animals of the HF series not only at the lesion site but under the skin of the whole face. Despite these severe conditions again TachoComb S exerted similar efficacy compared to TachoComb H.

Example 8

Neurosurgical Application of TachoComb H and TachoComb S: Brain Tissue Reaction and Hemostatic Effectiveness Fluid fibrin sealants are used on a large scale for hemostasis in neurosurgery. There exists no comprehensive published data on the brain tissue reaction to TachoComb® and the use of antifibrinolytic agents (i.e. aprotinin) is still controversial.

Objectives

The study design was focused on two major issues: The assessment of the short term local brain tissue reaction after application of TachoComb H (TCH) and TachoComb S (TCS) on cortical lesions as compared to blank control lesions (CL), using histological methods and modern imaging techniques.

The second objective was to study the hemostatic efficacy of TachoComb H and S products under normal coagulation (BTR Group) and after locally induced severe hyperfibrinolysis (HF Group), and to evaluate if aprotinin has any influence on the hemostatic qualities and adherence force of the preparation.

Material and Method

In a series of 22 young rabbits, three cortical lesions were made on each hemisphere. Twelve animals were assigned to the brain tissue reaction (BTR) group and 10 to the hyperfibrinolysis (HF) group.

In the BTR animals two of the lesions were filled with TachoComb H and TachoComb S, respectively, while the third was left empty as a control. The bleeding time was measured, and the occurrence of rebleeding due to induced arterial hypertension was monitored. The animals were killed on Days 3 and 7 after surgery and histological examination was performed. In three BTR animals magnetic resonance imaging for brain edema evaluation was performed on Day 3, just before euthanasia.

In the HF animals, in which a severe local hyperfibrinolytic status was previously induced with a recombinant tissue-plasminogen activator (rt-PA), all three lesions of one hemisphere were treated with TachoComb H and the other hemisphere with TachoComb S. Bleeding time was measured and in three animals histologic examination was performed on Day 3.

Results

Under normal coagulation (BTR animals), hemostasis with TCH and TCS was significantly faster (p<0.001) than with no hemostatic agent. It was demonstrated that there is no difference between the bleeding times of both products (p=0.294), but that these times are consistently shorter than those of the blank lesions (p<0.001).

During induced arterial hypertension rebleeding occurred in 1 of 24 TCH lesion, 3 of 24 TCS, and 19 of 24 control lesions. The presence of the hemostatic agent consistently prevented rebleeding during severely increased arterial pressure (Chi square=16.3; p>0.001). In turn, the absence of TCH or TCS during arterial pressure increase, showed an 80% risk of rebleeding occurrence.

The statistical analysis of the bleeding times in the hyperfibrinolysis group (HF animals) demonstrated no difference between the bleeding times for both products (signed-rank test: p=0.927 and T test: p=0.4102).

Finally, within a safety interval of 99.73% (D<3 sdD=ns) a significant difference between the hemostatic efficacy of the same product under both coagulation situations was ruled out.

Conclusion

TachoComb H and TachoComb S did not induce any specific histological changes in the brain tissue. Both products have a good brain parenchyma biocompatibility, as they did not induce more tissue reaction than the lesion alone. No adverse effects associated to the combination products were morphologically evident. Histological examination did not reveal differences between both products neither under normal, nor under severely disturbed coagulation. TachoComb H and S have the same hemostatic effectiveness and adhesive strength under both normal coagulation and hyperfibrinolysis. There is strong evidence that aprotinin has no influence on the hemostatic qualities and adherence force, even under severely disturbed coagulation.

As compared to the literature, TachoComb H and S establish much faster hemostasis than oxidized cellulose and collagen fleece.

What is claimed is:

1. A carrier coated with 4.3-6.7 mg fibrinogen/cm$^2$ and 1.5-2.5 I.U. thrombin/cm$^2$, wherein said carrier has a strength of adhesion of about 84-110 mbar, said carrier having at least one of the following physical properties:
   elasticity module in the range of 5-100 N/cm$^2$,
   density of 1-10 mg/cm$^3$,
   a chamber diameter of more than 0.75 mm and less than 4 mm, and
   a chamber diameter average below 3 mm; wherein
   said fibrinogen and said thrombin are solid fibrinogen and solid thrombin evenly distributed and fixed upon said carrier.

2. A carrier coated with 4.3-6.7 mg fibrinogen/cm$^2$ and 1.5-2.5 I.U. thrombin/cm$^2$, wherein said carrier has a strength of adhesion of about 84-110 mbar, said carrier having at least two of the following physical properties:
   elasticity module in the range of 5-100 N/cm$^2$,
   density of 1-10 mg/cm$^3$,
   a chamber diameter of more than 0.75 mm and less than 4 mm, and
   a chamber diameter average below 3 mm; wherein
   said fibrinogen and said solid thrombin are solid fibrinogen and solid thrombin evenly distributed and fixed upon said carrier.

* * * * *